United States Patent
Sinha et al.

(10) Patent No.: US 11,540,781 B2
(45) Date of Patent: Jan. 3, 2023

(54) MODELING A NEURONAL CONTROLLER EXHIBITING HUMAN POSTURAL SWAY

(71) Applicant: Tata Consultancy Services Limited, Mumbai (IN)

(72) Inventors: Aniruddha Sinha, Kolkata (IN); Oishee Mazumder, Kolkata (IN); Debatri Chatterjee, Kolkata (IN); Srinivasa Chakravarthy Vaddadi, Chennai (IN); Dipayan Biswas, Chennai (IN)

(73) Assignee: Tata Consultancy Services Limited, Mumbai (IN)

( * ) Notice: Subject to any disclaimer, the term of this patent is extended or adjusted under 35 U.S.C. 154(b) by 495 days.

(21) Appl. No.: 16/800,646

(22) Filed: Feb. 25, 2020

(65) Prior Publication Data
US 2020/0305800 A1    Oct. 1, 2020

(30) Foreign Application Priority Data
Mar. 29, 2019    (IN) .............................. 201921012442

(51) Int. Cl.
*A61B 5/00*    (2006.01)
*G16H 40/60*    (2018.01)
(Continued)

(52) U.S. Cl.
CPC .......... *A61B 5/7267* (2013.01); *A61B 5/1116* (2013.01); *A61B 5/1121* (2013.01);
(Continued)

(58) Field of Classification Search
CPC ... A61B 5/7267; A61B 5/1116; A61B 5/1121; A61B 5/4023; A61B 5/7203;
(Continued)

(56) References Cited

U.S. PATENT DOCUMENTS 9,221,177 B2 *   12/2015   Herr .................... B25J 9/1694
2019/0343446 A1 *  11/2019  Oddsson .............. A61B 5/1036

FOREIGN PATENT DOCUMENTS

| CN | 105549384 | 5/2016 | |
| CN | 107856035 | 3/2018 | |
| WO | WO-2018033591 A2 * | 2/2018 | ........... A61B 5/0488 |

OTHER PUBLICATIONS

Hamilton, Landon Douglas. "The influence of age and electrical nerve stimulation on motor function." A thesis submitted to the Faculty of the Graduate School of the University of Colorado in partial fulfillment of the requirement for the degree of Doctor of Philosophy Department of Integrative . . . (Year: 2018).*

(Continued)

*Primary Examiner* — Linh Giang Le
(74) *Attorney, Agent, or Firm* — Finnegan, Henderson, Farabow, Garrett & Dunner, LLP

(57) ABSTRACT

Conventionally, a neuronal controller located inside the central nervous system governing the maintenance of the upright posture of the human body is designed from a control system perspective using proportional-integral-derivative (PID) controllers, wherein human postural sway is modeled either along a sagittal plan or along a frontal plane separately resulting in limited insights on intricacies of a governing neuronal controller. Also, existing neuronal controllers using a reinforcement learning (RL) paradigm are based on complex actor-critic on-policy algorithms. Analyzing human postural sway is critical to detect markers for progression of balance impairments. The present disclosure facilitates modelling the neuronal controller using a simplified RL algorithm, capable of producing postural sway characteristics in both sagittal and frontal plane together. The Q-learning technique of the RL paradigm is employed (Continued)

for learning an optimal state-action value (Q-value) function for a tuneable Markov Decision Process (MDP) model.

15 Claims, 17 Drawing Sheets

(51) Int. Cl.
*G06N 20/00* (2019.01)
*A61B 5/11* (2006.01)
(52) U.S. Cl.
CPC .......... *A61B 5/4023* (2013.01); *A61B 5/7203* (2013.01); *A61B 5/725* (2013.01); *A61B 5/7225* (2013.01); *G06N 20/00* (2019.01); *G16H 40/60* (2018.01)
(58) Field of Classification Search
CPC ..... A61B 5/7225; A61B 5/725; A61B 5/1122; A61B 5/4082; A61B 5/72; A61B 5/7246; G06N 20/00; G16H 40/60; G16H 50/70; G16H 50/50

See application file for complete search history.

(56) References Cited

OTHER PUBLICATIONS

Hengst, B. "Reinforcement Learning Inspired Disturbance Rejection and Nao Bipedal Locomotion," *The 10th Workshop on Humanoid Soccer Robots, 15th IEEE-RAS International Conference on Humanoid Robots*, Seoul, Korea, Nov. 3, 2015; 6 pages.

Ghanbari, A. et al. (Dec. 2015). Neural Network Reinforcement Learning for Walking Control of a 3-Link Biped Robot, *IACSIT International Journal of Engineering and Technology*, vol. 7, No. 6; pp. 449-452.

\* cited by examiner

302 — modeling the neuronal controller in the form of a Reinforcement Learning (RL) agent based on an inverted pendulum with 1 Degree Of Freedom (1DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately 304 — deriving dynamical equations of a Spherical Inverted Pendulum (SIP) with respect to the global coordinate system, wherein the SIP represents a second mechanical model of the human body that exhibits postural sway along both the frontal plane and the sagittal plane together, wherein the dynamical equations are derived by using Lagrange's equations with two independent state variables ($\theta x$ and $\theta y$) being angular deviation of the SIP about a pivot joint thereof and along $x$ and $y$ axes respectively of the global coordinate system, wherein the pivot joint characterizes an ankle joint of the human body 306 — modeling the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller matches the postural sway characteristics of one or more control subjects, wherein the set of parameters include parameters of the MDP model and parameters associated with physiology of the human body

MODELING A NEURONAL CONTROLLER EXHIBITING HUMAN POSTURAL SWAY

PRIORITY CLAIM

This U.S. patent application claims priority under 35 U.S.C. § 119 to: Indian Patent Application No. 201921012442, filed on 29 Mar. 2019. The entire contents of the aforementioned application are incorporated herein by reference.

TECHNICAL FIELD

The disclosure herein generally relates to postural sway analyses, and, more particularly, to systems and computer implemented methods for modeling a neuronal controller exhibiting human postural sway.

BACKGROUND

Analyzing human postural sway is critical to detect markers for progression of balance impairments. Typically, balance impairments are caused by altered functions of the central nervous system or sensory or motor functions which may be due to age or pathology. Parkinson's disease and peripheral neuropathy may be deciphered by analyzing the postural sway. Conventionally, a neuronal controller located inside the central nervous system governing the maintenance of the upright posture of the human body is designed from a control system perspective using one or more proportional-integral-derivative (PID) controllers, wherein human postural sway is modeled either along a sagittal plan or along a frontal plane separately resulting in limited insights on intricacies of a governing neuronal controller. Some attempts have also been made to model the neuronal controller using a reinforcement learning (RL) paradigm based on complex actor-critic on-policy algorithms.

SUMMARY

Embodiments of the present disclosure present technological improvements as solutions to one or more of the above-mentioned technical problems recognized by the inventors in conventional systems.

In an aspect, there is provided a processor implemented method for modeling a neuronal controller exhibiting human postural sway comprising the steps of: modeling, by one or more hardware processors, the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately; deriving, by the one or more hardware processors, dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables ($\theta x$ and $\theta y$) being angular deviation of the SIP about a pivot joint and along x and y axes respectively of the global coordinate system, wherein the pivot joint characterizes an ankle joint of the human body; and modeling, by the one or more hardware processors, the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

In another aspect, there is provided a system for modeling a neuronal controller exhibiting human postural sway, the system comprising: one or more data storage devices operatively coupled to one or more hardware processors and configured to store instructions configured for execution by the one or more hardware processors to: model the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately; derive dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables ($\theta x$ and $\theta y$) being angular deviation of the SIP about a pivot joint and along x and y axes respectively of the global coordinate system, wherein the pivot joint characterizes an ankle joint of the human body; and model the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

In yet another aspect, there is provided a computer program product comprising a non-transitory computer readable medium having a computer readable program embodied therein, wherein the computer readable program, when executed on a computing device, causes the computing device to: model the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately; derive dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables (θx and θy) being angular deviation of the SIP about a pivot joint and along x and y axes respectively of the global coordinate system, wherein the pivot joint characterizes an ankle joint of the human body; and model the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

In accordance with an embodiment of the present disclosure, the Q-learning technique is configured to learn to generate a torque representing an action for each state of the inverted pendulum by: receiving proprioceptive inputs in the form of angle and angular velocity of the pivot joint of the inverted pendulum; and generating the torque at the pivot joint of the inverted pendulum based on the received proprioceptive inputs to maintain an upright posture of the inverted pendulum.

In accordance with an embodiment of the present disclosure, the one or more hardware processors are configured to perform the step of modeling a neuronal controller by reproducing the Center Of Pressure (COP) characteristics in the human body either along the sagittal or along the frontal plane separately in accordance with a dynamic equation based on overall mass m of the human body being concentrated at the point of Center Of Mass (COM) located at the $2^{nd}$ lumbar vertebrae of the human body, an approximate height L of the $2^{nd}$ lumbar vertebrae, moment of inertia of the inverted pendulum I, angle of the inverted pendulum θ with respect to the direction of gravity, gravitational acceleration g, a stiffness constant K and a damping constant B, wherein the stiffness constant and the damping constant denote pivot joint properties of the inverted pendulum.

In accordance with an embodiment of the present disclosure, the parameters of the MDP model include: $n_θ$ representing resolution of states in θ domain (from $θ_{max}$ to $-θ_{max}$); $n_{\dot{θ}}$ representing resolution of states in $\dot{θ}$ domain (from $\dot{θ}_{max}$ to $-\dot{θ}_{max}$); $n_A$ representing resolution of states in τ domain (from $τ_{max}$ to $-τ_{max}$); $τ_{max}$ representing the maximum torque exertable on the pivot joint or the boundary of the τ domain; $θ_{max}$ representing the boundary of the θ domain; $\dot{θ}_{max}$ representing a finite boundary of the $\dot{θ}$ domain; $p_a$ representing property of a curve from which torque values in the τ domain is sampled; $p_θ$ representing property of a curve from which boundaries of states of the θ domain is sampled; and $p_{\dot{θ}}$ representing property of a curve from which boundaries of the states of the $\dot{θ}$ domain is sampled; and the parameters associated with physiology of the human body include: White Gaussian Noise (WGN) added to the generated torque to represent a real world noisy biological system; filtering factor (λ) added to portray signaling characteristics of a neuromuscular junction; and Scaling Factor (SF) introduced to scale down the magnitude of the generated torque for each state of the inverted pendulum after the training of the RL agent is completed, wherein completion is of the training is represented by a balanced SIP.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3 illustrates an exemplary flow diagram of a computer implemented method for modeling a neuronal controller exhibiting human postural sway, in accordance with an embodiment of the present disclosure.

DETAILED DESCRIPTION

Figure 1:
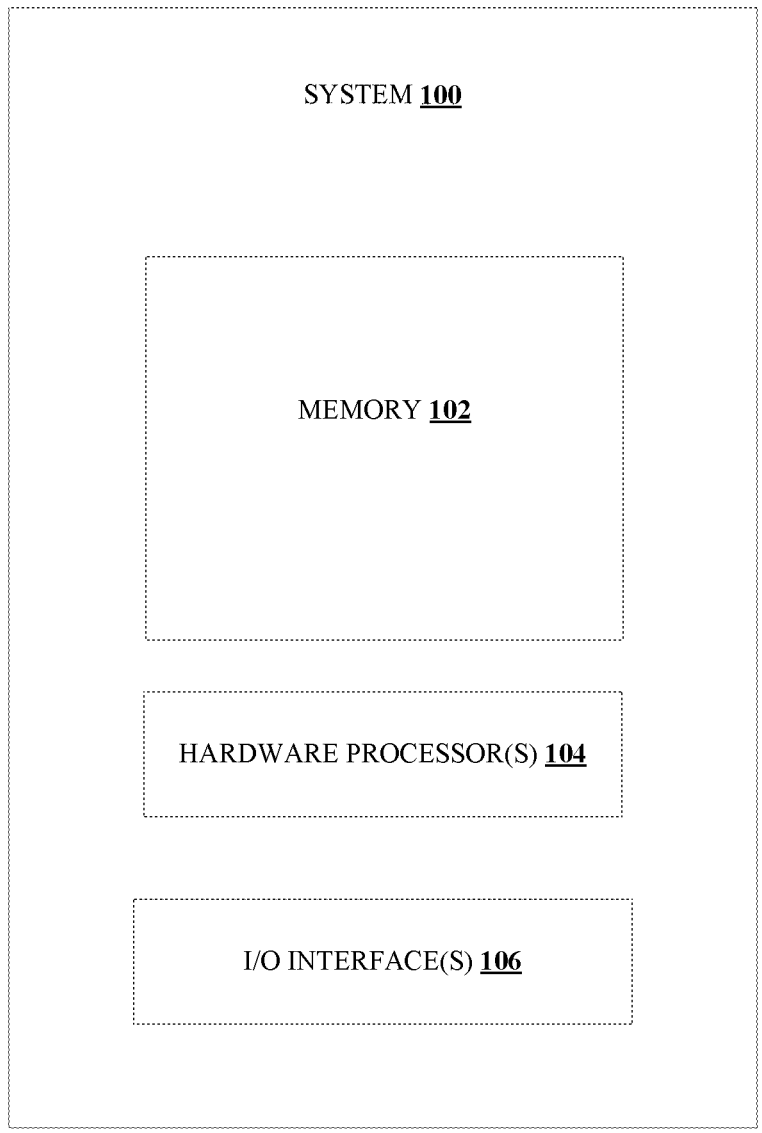
FIG. 1 illustrates an exemplary block diagram of a system for modeling a neuronal controller exhibiting human postural sway, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

State of the art techniques for analyzing human postural sway, model the human postural sway either along a sagittal plane or along a frontal plane separately. Modeling separately along the anatomical planes only give lower dimensional projection of higher dimensional dynamics which in turn compromises the overall picture portraying the human postural sway. Also, the attempts were directed to designing the neuronal controller located inside the central nervous system governing the maintenance of the upright posture of the human body from a control system perspective using PID controllers. Using PID controller only gives rise to limited set of parameters with very less neurophysiological significance. Some attempts to model the neuronal controller using Reinforcement Learning (RL) paradigm were actor-critic on-policy algorithms that address optimization of two redundant parallel entities viz., the 'policy' and the 'actor' which was relatively complex and computationally inefficient.

The methods and systems of the present disclosure firstly facilitate designing the neuronal controller using a simplified RL algorithm capable of producing diverse sway characteristics either in the sagittal plane or in the front plane separately using a simple inverted pendulum representing a mechanical model of a human body. Dynamical equations of a Spherical Inverted Pendulum (SIP) are derived with respect to a global coordinate system. The modeled neuronal controller is then adapted to exhibit diverse sway characteristics in the sagittal plane and in the front plane together. The present disclosure also provides parameters which enable the sway characteristics exhibited by the modeled neuronal controller to be close to normal and pathological conditions seen in the real world. Systems and methods of the present disclosure find application in analyzing the postural balance of a subject so that subject specific rehabilitation protocols may be recommended.

Referring now to the drawings, and more particularly to FIG. 1 through FIG. 9D, where similar reference characters denote corresponding features consistently throughout the figures, there are shown preferred embodiments and these embodiments are described in the context of the following exemplary system and/or method.

FIG. 1 illustrates an exemplary block diagram of a system 100 for modeling a neuronal controller exhibiting human postural sway, in accordance with an embodiment of the present disclosure. In an embodiment, the system 100 includes one or more hardware processors 104, communication interface device(s) or input/output (I/O) interface(s) 106, and one or more data storage devices or memory 102 operatively coupled to the one or more processors 104. The one or more processors 104 can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
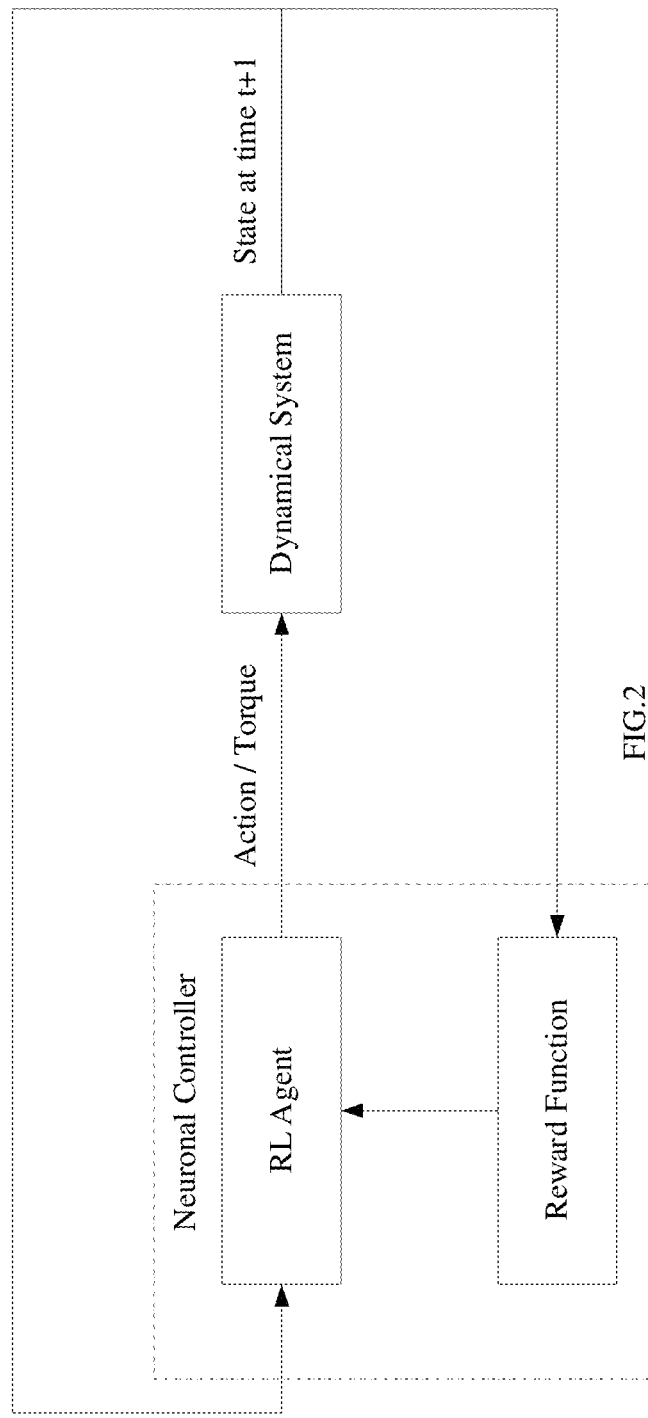
FIG. 2 illustrates a high level architecture enabling a method for modeling a neuronal controller exhibiting human postural sway, in accordance with an embodiment of the present disclosure.

FIG. 2 illustrates a high level architecture enabling a method for modeling a neuronal controller exhibiting human postural sway, in accordance with an embodiment of the present disclosure. FIG. 3 illustrates an exemplary flow diagram of a computer implemented method 300 for modeling a neuronal controller exhibiting human postural sway, in accordance with an embodiment of the present disclosure. In an embodiment, the system 100 includes one or more data storage devices or memory 102 operatively coupled to the one or more processors 104 and is configured to store instructions configured for execution of steps of the method 300 by the one or more processors 104. The steps of the method 300 will now be explained in detail with reference to the components of the system 100 of FIG. 1 and the architecture of FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In accordance with an embodiment of the present disclosure, the one or more processors 104 are configured to model, at step 302, the neuronal controller in the form of a Reinforcement Learning (RL) agent based on an inverted pendulum with 1 Degree of Freedom (1 DOF) representing a first mechanical model of a human body in the form of a dynamical system. In an embodiment, the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along the sagittal plane or along the frontal plane separately.

The modeling of the MDP for the RL agent, in accordance with an embodiment of the present disclosure is performed as described herein after. Markov decision process contains the elements [S, A, P(ś|s, a), E[r|s, á, s]γ], wherein S represents a set of states, A represents a set of actions, P(ś|s, a) represents a transition probability, γ represents a discount factor and E[r|s, á, s] represents an expected reward for a current state s, immediate action a and next state ś. The model based algorithm has no stochasticity associated with state transition. Accordingly, given a particular state s (in terms of $\theta$ and $\dot{\theta}$) and action a (in terms of torque at a pivot joint), system dynamics reveal an immediate next state. A reward policy or a reward function (used interchangeably in the context of the present disclosure) is also modeled deterministically. The set of states S, the set of actions A and the reward policy are modeled as described hereinafter.

Modeling the set of actions A: The actions are sampled using a curve represented as:

$$y = \tau_{max} a|x|^p \text{ for } x \geq 0 \qquad (1)$$
$$y = -\tau_{max} a|x|^p \text{ for } x < 0$$
$$a = \frac{1}{\left(\frac{n_A - 1}{2}\right)^p},$$

where $n_A$ represents number of actions, p represents an exponent that defines the characteristics of a curve represented in equation 1. and $\tau_{max}$ represents a maximum torque applied to the pivot joint. Let set, $X_A = \{\text{all integers}|-(n_A-1)/2 \leq n \leq (n_A-1)/2\}$, where $x_a \in X_A$ and n denotes an integer number. To obtain, $n_A$ number of actions, the curve represented by equation (1) is sampled for all integer values in the range $-(n_A-1)/2 \leq n \leq (n_A-1)/2$ for all elements of the set $X_A$ or $A = \{\text{all y from equation } (1)|x \in X_A\}$.

Modeling the set of States (S): The system state comprises of two state variables $\theta$ and $\dot{\theta}$. The scope of the state variable $\theta$ spans from $-\theta_{max}$ to $\theta_{max}$ and is represented as $\theta_{span}$. Since the present disclosure deals with discrete MDP, the $\theta$ and $\dot{\theta}$ space is discretized by defining boundaries. Boundaries of 'sub-states' in $\theta$ space are sampled from a curve represented by equation (2) below.

$$y = \theta_{max} a|x|^p \text{ for } x \geq 0 \qquad (2)$$
$$y = -\theta_{max} a|x|^p \text{ for } x < 0$$
$$a = \frac{1}{\left(\frac{n_\theta + 1}{2}\right)^p},$$

where $n_\theta$ represents number of sub-states in the $\theta$ space inside $\theta_{span}$ and wherein $n_\theta$ is chosen to be an odd integer. If a set $$X_\theta = \left\{\text{all integers} \left| -\frac{n_\theta + 1}{2} \leq n \leq \frac{n_\theta + 1}{2} \text{ and } x_\theta \neq 0\right.\right\},$$

where $x_\theta \in X_\theta$, $n_\theta + 1$ number of boundaries required to define $n_\theta$ number of states, may be samples from equation (2) for all elements of the set $X_\theta$. The set containing these boundaries may be represented as given below.

$\theta_{SB} = \{\text{all y from equation } (2)|x \in X_\theta\}$ or, $\theta_{SB_i} \in \theta_{SB}$ where, $i \in X_\theta$ On similar lines, scope of the state variable $\dot{\theta}$ spans from $-\infty$ to $\infty$. Sub-state $-1$ spans from $-\infty$ to $-\dot{\theta}_{max}$ and state $-n_{\dot{\theta}}$ spans from $\dot{\theta}_{max}$ to $\infty$, where $n_{\dot{\theta}}$ represents number of sub-states in the $\dot{\theta}$ domain. From $-\dot{\theta}_{max}$ to $\dot{\theta}_{max}$, there are $n_{\dot{\theta}} - 2$ states, boundaries of which are defined by taking $n_{\dot{\theta}} - 1$ samples of all elements of a set $$X_{\dot{\theta}} = \left\{\text{all integers} \left| -\frac{n_{\dot{\theta}} - 1}{2} \leq x_{\dot{\theta}} \leq \frac{n_{\dot{\theta}} - 1}{2} \text{ and } x_{\dot{\theta}} \neq 0\right.\right\},$$

where $x_{\dot{\theta}} \in X_{\dot{\theta}}$ from a curve represented by equation (3) below.

$$y = \dot{\theta}_{max} a|x|^p \text{ for } x \geq 0 \qquad (3)$$
$$y = -\dot{\theta}_{max} a|x|^p \text{ for } x < 0$$
$$a = \frac{1}{\left(\frac{n_{\dot{\theta}} - 1}{2}\right)^p},$$

where $n_{\dot{\theta}}$ represents number of sub-states in the $\dot{\theta}$ space inside $\theta_{span}$.

Also, the set containing these boundaries may be represented as given below.

$\dot{\theta}_{SB} = \{\text{all y from equation } (3)|x \in X_{\dot{\theta}}\}$ or, $\dot{\theta}_{SB_i} \in \dot{\theta}_{SB}$ where, $i \in X_{\dot{\theta}}$ If $S_\theta$ is a set of sub-states corresponding to the state variable $\theta$, then, $$S_\theta = \left\{S_{\theta_i} \left| i \in \left\{\text{all integers} \left| -\frac{n_\theta - 1}{2} \leq n \leq \frac{n_\theta - 1}{2}\right.\right\}\right.\right\},$$

wherein the $i^{th}$ element of the set spans the $\theta$ space as shown below.

$\theta_{SB_{i-1}} \leq \theta < \theta_{SB_i}$ for $i<0$;
$\theta_{SB_{i-1}} \leq \theta < \theta_{SB_{i+1}}$ for $i=0$;
$\theta_{SB_i} \leq \theta < \theta_{SB_{i+1}}$ for $i>0$;

Similarly, the set corresponding to the state variable $\dot{\theta}$, $$S_{\dot{\theta}} = \left\{S_{\dot{\theta}_i} \left| i \in \left\{\text{all integers} \left| -\frac{n_{\dot{\theta}} - 1}{2} \leq n \leq \frac{n_{\dot{\theta}} - 1}{2}\right.\right\}\right.\right\},$$

And the $i^{th}$ element of the set spans the $\dot{\theta}$ space as shown below.

$\dot{\theta} < \dot{\theta}_{SB_i}$ for $i = -\frac{n_{\dot{\theta}} - 1}{2}$;

$\dot{\theta} > \dot{\theta}_{SB_i}$ for $i = \frac{n_{\dot{\theta}} - 1}{2}$;

$\dot{\theta}_{SB_{i-1}} \leq \dot{\theta} < \dot{\theta}_{SB_i}$ for $-\frac{n_{\dot{\theta}} - 1}{2} < i < 0$ $\dot{\theta}_{SB_{i-1}} \leq \dot{\theta} < \dot{\theta}_{SB_{i+1}}$ for $i = 0$ $\dot{\theta}_{SB_i} \leq \dot{\theta} < \dot{\theta}_{SB_{i+1}}$ for $0 < i < \frac{n_{\dot{\theta}} - 1}{2}$ The elements of the set S is a combination of elements of the sets $S_\theta$ and $S_{\dot{\theta}}$ respectively.

Modeling the Reward (E[r|ś,a,s]): In accordance with the present disclosure, the reward policy or the reward function may be modeled in multiple approaches as discussed hereinafter.

Reward policy-1: The RL agent gets a reward of +1 when ś (state of the system at t+1) falls inside $S_{\theta_0}$ (which spans between two nearest $\theta$ boundaries on either side of $\theta=0$ as specified in $\theta_{SB}$) i.e. the reward states comes under the set:

$$S_R = \left\{ \left(S_{\theta_0}, S_{\dot\theta_{-\frac{n_{\dot\theta}-1}{2}}}\right), \left(S_{\theta_0}, S_{\dot\theta_{-\frac{n_{\dot\theta}+1}{2}}}\right), \right.$$
$$\left. \ldots, \left(S_{\theta_0}, S_{\dot\theta_0}\right), \ldots, \left(S_{\theta_0}, S_{\dot\theta_{\frac{n_{\dot\theta}-3}{2}}}\right), \left(S_{\theta_0}, S_{\dot\theta_{\frac{n_{\dot\theta}-1}{2}}}\right) \right\}$$

Reward policy-2: The RL agent gets a reward of +1 when $\acute{s}$ falls inside the sub-state $S_{\theta_0}$ and $S_{\dot\theta_0}$ simultaneously, in which case the reward state is only one state out of all the elements of the set S. So, $S_R=\{(S_{\theta_0}, S_{\dot\theta_0})\}$. The significance of this reward policy is that it encodes the objective of making the inverted pendulum reach the vertical state and stay in the same state.

Reward policy-3: A Gaussian reward policy over the state space is represented as follows:

$$r = e^{-\left(\frac{\theta}{\sigma_\theta}\right)^2 - \left(\frac{\dot\theta}{\sigma_{\dot\theta}}\right)^2}$$

where $\sigma_\theta$ and $\sigma_{\dot\theta}$ are standard deviations of the Gaussian reward policy over the $\theta$ and $\dot\theta$ dimensions respectively. The lower values of $\sigma_\theta$ and $\sigma_{\dot\theta}$ reduce the scope of getting the reward. Also, this is a continuous reward policy as opposed to the Reward policy-1 and the Reward policy-2.

Reward policy-4: A negative reward policy is also adapted frequently where the RL agent gets a negative reward of −10 or a punishment of 10 when the inverted pendulum falls out of $\theta_{max}$ and $\dot\theta_{max}$.

Transitional probability ($P(\acute{s}|s,a)$) and discount factor ($\gamma$): Considering the system dynamics are known, the need for finding the transitional probability is averted. The discount factor ($\gamma$) which is a parameter of temporal difference learning, is chosen to be 0.1.

In accordance with an embodiment, the parameters of the MDP model may include:

$n_\theta$ representing resolution of states in $\theta$ domain (from $\theta_{max}$ to $-\theta_{max}$);

$n_{\dot\theta}$ representing resolution of states in $\dot\theta$ domain (from $\dot\theta_{max}$ to $-\dot\theta_{max}$);

$n_A$ representing resolution of states in $\tau$ domain (from $\tau_{max}$ to $-\tau_{max}$);

$\tau_{max}$ representing the maximum torque exertable on the pivot joint or the boundary of the $\tau$ domain;

$\theta_{max}$ representing the boundary of the $\theta$ domain;

$\dot\theta_{max}$ representing a finite boundary of the $\dot\theta$ domain;

$p_a$ representing property of a curve from which torque values in the $\tau$ domain is sampled;

$p_\theta$ representing property of a curve from which boundaries of states of the $\theta$ domain is sampled; and $p_{\dot\theta}$ representing property of a curve from which boundaries of the states of the $\dot\theta$ domain is sampled.

Increasing $n_\theta$, $n_{\dot\theta}$, $n_A$ parameter values gives more resolution to the system states (S) and actions (A), at the cost of increased training time for the RL agent.

In an embodiment, the Q-learning technique, which is an off-policy algorithm for temporal difference learning, is configured to learn to generate a torque representing an action for each state of the inverted pendulum by receiving proprioceptive inputs in the form of angle and angular velocity of the pivot joint of the inverted pendulum; and generating the torque at the pivot joint of the inverted pendulum based on the received proprioceptive inputs to maintain an upright posture of the inverted pendulum. In an embodiment of the present disclosure, the optimal state-action value (Q-value) function is in the form of a look-up table.

In accordance with the present disclosure, the algorithm for Q-learning technique may be represented as given below:

Initialize $Q(s, a)$ arbitrarily

Repeat (for each episode):

Initialize $s$

Repeat (for each step of the episode):

Choose $a$ from $s$ using a policy derived from $Q$ (e.g., $\varepsilon$-greedy)

Take action $a$, observe $r$, $\acute{s}$ $$Q(s, a) \leftarrow (1-\alpha)Q(s, a) + \alpha\left(r + \gamma * \max_{\acute{s}} Q(\acute{s}, \acute{a})\right)$$

$s \leftarrow \acute{s}$

Until $s$ is terminal, where $\alpha$ represents a learning rate, value of which typically lies between 0 and 1. $\alpha=0$ means $Q(s, \alpha)$ is not updated or there is no learning, whereas $\alpha=1$ means $Q(s, \alpha)$ is updated depending on an expected total reward achieved in a recent episode and is independent of a previous $Q(s, \alpha)$ value for a particular state and action. Also, $\varepsilon$ represents an exploration factor associated with the $\varepsilon$-greedy policy that aims to define balance between exploration and exploitation of immediate reinforcement learning. A value of $\varepsilon$ near 0 ensures the RL agent prefers exploitation over exploration and vice versa.

The s and a are the current state and immediate action taken at time t and $\acute{s}$ and $\acute{a}$ are the state and the action taken at time t+1 respectively. It is proven that once the Q values are learnt for a significant number of episodes under the $\varepsilon$-greedy policy, the Q-learning algorithm converges to close approximation of optimal state-action value function ($Q^*(s, \alpha)$) with probability 1. Once the RL agent has learnt the Q values for significant number of episodes, the RL agent is ready for exploitation only (means $\varepsilon=0$), i.e. at a given state it will choose the action with maximum Q value by $$\arg\max_a Q(s, a).$$

Figure 4:
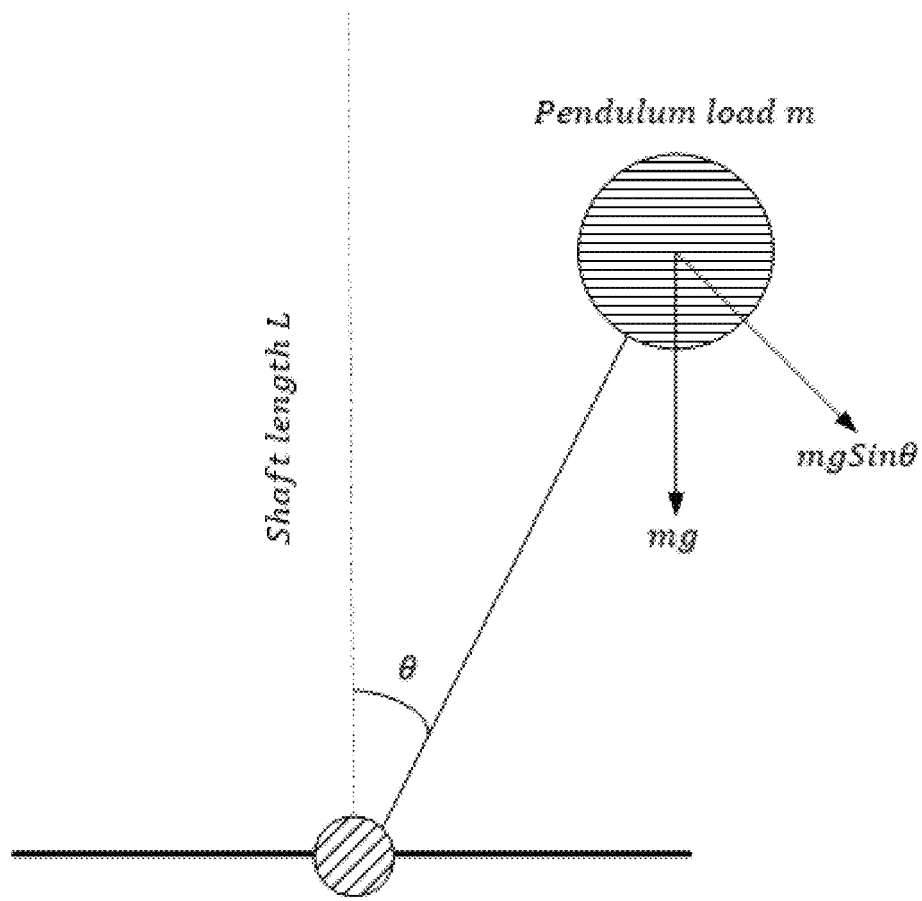
FIG. 4 illustrates a 1 Degree Of Freedom (1 DOF) inverted pendulum representing a free body diagram of a simplified human body in the sagittal plane, in accordance with an embodiment of the present disclosure.

In accordance with an embodiment of the present disclosure, the Center Of Pressure (COP) characteristics in the human body either along the sagittal or along the frontal plane are reproduced separately in accordance with a dynamical equation based on overall mass of the human body being concentrated at the point of Center Of Mass (COM) located at the $2^{nd}$ lumbar vertebrae of the human body, an approximate height of the $2^{nd}$ lumbar vertebrae, moment of inertia of the inverted pendulum, angle of the inverted pendulum with respect to the direction of gravity, gravitational acceleration, a stiffness constant and a damping constant, wherein the stiffness constant and the damping constant denote pivot joint properties of the inverted pendulum. FIG. 4 illustrates a 1 Degree Of Freedom (1 DOF) inverted pendulum representing a free body diagram of a simplified human body in the sagittal plane, in accordance with an embodiment of the present disclosure. In an embodiment, the dynamical equation may be represented as:

$$I\frac{d^2\theta}{dt^2} = \tau + mgL\sin\theta - B\dot\theta - K\theta \text{ where } I = mL^2, \quad (4)$$

and
where m represents the overall mass of the human body being concentrated at the point of Center Of Mass (COM) located at the $2^{nd}$ lumbar vertebrae of the human body;
L represents the approximate height of the $2^{nd}$ lumbar vertebrae;
$\theta$ represents angle of the inverted pendulum;
g represents gravitational acceleration;
I represents moment of inertia of the inverted pendulum;
K represents the stiffness constant; and
B represents the damping constant.

Figure 5:
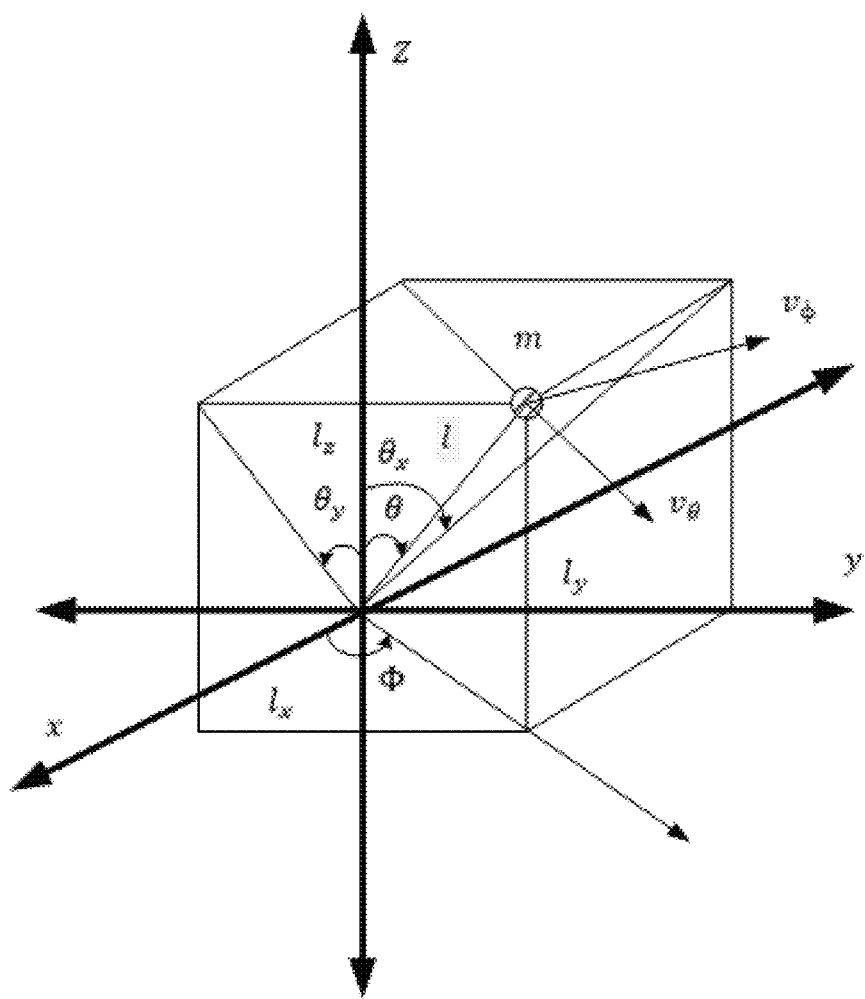
FIG. 5 illustrates a Spherical Inverted Pendulum (SIP) having 2 DOF with two state variables, θx and θy, in accordance with an embodiment of the present disclosure.

In accordance with an embodiment of the present disclosure, the one or more processors 104 are configured to derive, at step 304, dynamical equations of a Spherical Inverted Pendulum (SIP) with respect to the global coordinate system. In accordance with the present disclosure, the SIP represents a second mechanical model of the human body that is capable of exhibiting postural sway along both the frontal plane and the sagittal plane together. In an embodiment, the dynamical equations are derived by using Lagrange's equations with two independent state variables ($\theta x$ and $\theta y$) that represent angular deviation of the SIP about a pivot joint and along x and y axes respectively of the global coordinate system, wherein the pivot joint characterizes an ankle joint of the human body. FIG. 5 illustrates an SIP having 2 DOF with the two state variables, $\theta x$ and $\theta y$, in accordance with an embodiment of the present disclosure. As the reference plan passes through the origin, there are two sets of equations for the SIP, a set representing above and below the reference planes respectively. In FIG. 5, ($l_x$, $l_y$, $l_z$) is a Cartesian co-ordinate system representation of the position of the pendulum mass. m and l represent pendulum mass and length of the shaft of the SIP respectively.

In accordance with the present disclosure, the dynamical equations are derived as described hereinafter. The Lagrange's equations are as given below.

$$\frac{\partial}{\partial t}\left(\frac{\partial L}{\partial \dot\theta_x}\right) - \frac{\partial L}{\partial \theta_x} = \tau_x \quad (5)$$

$$\frac{\partial}{\partial t}\left(\frac{\partial L}{\partial \dot\theta_y}\right) - \frac{\partial L}{\partial \theta_y} = \tau_y$$

Where L is the Lagrangian, given by:

$$L = K - V \quad (6)$$

$$\text{Kinetic energy} = \frac{1}{2}m(v_x^2 + v_y^2 + v_z^2) \quad (7)$$

$$V = \text{Potential energy} = mgl_z \quad (8)$$

where, $$v_x = \frac{\partial l_x}{\partial t}; v_y = \frac{\partial l_y}{\partial t}; v_z = \frac{\partial l_z}{\partial t} \quad (9)$$

-continued
$$l_x = l\sin\theta\cos\phi; l_y = l\sin\theta\sin\phi; l_z = l\cos\theta \quad (10)$$

Representing $\theta$ and $\phi$ in terms of $\theta_x$ and $\theta_y$:

$$\tan\theta = \frac{\sqrt{l_x^2 + l_y^2}}{l_z} \text{ and } \tan\phi = \frac{l_y}{l_x} \text{ where } \tan\theta_y = \frac{l_x}{l_z} \text{ and }$$

$$\tan\theta_x = \frac{l_y}{l_z}$$

Therefore, $$\tan\theta = \sqrt{\left(\frac{l_x}{l_z}\right)^2 + \left(\frac{l_y}{l_z}\right)^2} = \sqrt{\tan^2\theta_y + \tan^2\theta_x} \quad (11)$$

And $$\tan\phi = \frac{l_y}{l_x} = \frac{\frac{l_y}{l_z}}{\frac{l_x}{l_z}} = \frac{\tan\theta_x}{\tan\theta_y} \quad (12)$$

From equations (11) and (12), $$\cos\theta = \frac{1}{\sqrt{1 + \tan^2\theta_x + \tan^2\theta_y}}; \sin\theta = \sqrt{\frac{\tan^2\theta_x + \tan^2\theta_y}{1 + \tan^2\theta_x + \tan^2\theta_y}}$$

$$\cos\phi = \frac{\tan\theta_y}{\sqrt{\tan^2\theta_x + \tan^2\theta_y}}; \sin\phi = \frac{\tan\theta_x}{\sqrt{\tan^2\theta_x + \tan^2\theta_y}}$$

Further, in accordance with the present disclosure, kinetic energy, potential energy and Lagrangian may be derived as below. Using the values of $\cos\theta$, $\sin\theta$, $\cos\phi$ and $\sin\phi$ in equation (10), $$l_x = \frac{l\tan\theta_y}{\sqrt{1 + \tan^2\theta_x + \tan^2\theta_y}}; \quad (13)$$

$$l_y = \frac{l\tan\theta_x}{\sqrt{1 + \tan^2\theta_x + \tan^2\theta_y}};$$

$$l_z = \pm\frac{l}{\sqrt{1 + \tan^2\theta_x + \tan^2\theta_y}}$$

Plugging equation (13) in equation (9) gives the velocity components along the x, y, and z axes as follows:

$$v_x = \frac{\partial l_x}{\partial t} = l\frac{\sec^2\theta_x\sec^2\theta_y\dot\theta_y - \tan\theta_x\tan\theta_y\sec^2\theta_x\dot\theta_x}{(1 + \tan^2\theta_x + \tan^2\theta_y)^{3/2}} \quad (14)$$

$$v_y = \frac{\partial l_y}{\partial t} = l\frac{\sec^2\theta_x\sec^2\theta_y\dot\theta_x - \tan\theta_x\tan\theta_y\sec^2\theta_y\dot\theta_y}{(1 + \tan^2\theta_x + \tan^2\theta_y)^{3/2}}$$

$$v_z = \frac{\partial l_z}{\partial t} = -l\frac{\tan\theta_x\sec^2\theta_x\dot\theta_x + \tan\theta_y\sec^2\theta_y\dot\theta_y}{(1 + \tan^2\theta_x + \tan^2\theta_y)^{3/2}}$$

The kinetic energy and the potential energy derived from equations (7), (8), (13) and (14) may be represented as below.

$$K = \frac{1}{2}ml^2 \frac{\sec^2\theta_x \sec^2\theta_y \left[\dot{\theta}_x^2 + \dot{\theta}_y^2 + \left(\tan\theta_x\dot{\theta}_x - \tan\theta_y\dot{\theta}_y\right)^2\right]}{\left(1 + \tan^2\theta_x + \tan^2\theta_y\right)^2} \quad (15)$$

$$V = \pm \frac{mgl}{\sqrt{1 + \tan^2\theta_x + \tan^2\theta_y}}; \; +ve \text{ for } \theta \le 90° \text{ and}$$

$$-ve \text{ for } \theta \ge 90°$$

In accordance with an embodiment of the present disclosure, using the kinetic energy and potential energy in equation (6), provides the Lagrangian (L) and plugging the Lagrangian in equation (5), the dynamical equations of the SIP are represented as:

for θ=0 to 90°, θ being the polar or zenith angle of the spherical coordinate system, $$\ddot{\theta}_x = \frac{1}{\left(\sec^2\theta_y + \tan^2\theta_x\right)^2} \quad (16)$$

$$\left[\frac{1}{2}(1 + 3\cos2\theta_x - \cos2\theta_y + \cos2\theta_x\cos2\theta_y)\sec^2\theta_x\sec^4\theta_y\tan\theta_y\dot{\theta}_x\dot{\theta}_y + \right.$$

$$(1 + \cos2\theta_x + \cos2\theta_y + \cos2\theta_x\cos2\theta_y)\sec^2\theta_x\sec^4\theta_y\tan\theta_y\tan^2\theta_x\dot{\theta}_x\dot{\theta}_y -$$

$$\left. 2\dot{\theta}_x^2\tan\theta_x\tan^2\theta_y\left(\sec^2\theta_y + \tan^2\theta_x\right)\right] + \frac{g}{l}\frac{\tan\theta_x}{\sec^2\theta_x}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_y\tan\theta_x\tan\theta_y + \tau_y\sec^2\theta_y\right),$$

$$\ddot{\theta}_y = \frac{1}{\left(\sec^2\theta_y + \tan^2\theta_x\right)^2} \quad (17)$$

$$\left[\frac{1}{2}(1 + 3\cos2\theta_y - \cos2\theta_x + \cos2\theta_x\cos2\theta_y)\sec^2\theta_y\sec^4\theta_x\tan\theta_x\dot{\theta}_x\dot{\theta}_y + \right.$$

$$(1 + \cos2\theta_x + \cos2\theta_y + \cos2\theta_x\cos2\theta_y)\sec^2\theta_y\sec^4\theta_x\tan\theta_x\tan^2\theta_y\dot{\theta}_x\dot{\theta}_y -$$

$$\left. 2\dot{\theta}_y^2\tan\theta_y\tan^2\theta_x\left(\sec^2\theta_y + \tan^2\theta_x\right)\right] + \frac{g}{l}\frac{\tan\theta_y}{\sec^2\theta_y}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_x\tan\theta_x\tan\theta_y + \tau_y\sec^2\theta_x\right);$$

for θ > 90°, $$\ddot{\theta}_x = \frac{1}{\left(\sec^2\theta_y + \tan^2\theta_x\right)^2} \quad (18)$$

$$\left[\frac{1}{2}(1 + 3\cos2\theta_x - \cos2\theta_y + \cos2\theta_x\cos2\theta_y)\sec^2\theta_x\sec^4\theta_y\tan\theta_y\dot{\theta}_x\dot{\theta}_y + \right.$$

$$(1 + \cos2\theta_x + \cos2\theta_y + \cos2\theta_x\cos2\theta_y)\sec^2\theta_x\sec^4\theta_y\tan\theta_y\tan^2\theta_x\dot{\theta}_x\dot{\theta}_y -$$

$$\left. 2\dot{\theta}_x^2\tan\theta_x\tan^2\theta_y\left(\sec^2\theta_y + \tan^2\theta_x\right)\right] - \frac{g}{l}\frac{\tan\theta_x}{\sec^2\theta_x}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_y\tan\theta_x\tan\theta_y + \tau_x\sec^2\theta_y\right) \text{ and}$$

$$\ddot{\theta}_y = \frac{1}{\left(\sec^2\theta_y + \tan^2\theta_x\right)^2} \quad (19)$$

$$\left[\frac{1}{2}(1 + 3\cos2\theta_y - \cos2\theta_x + \cos2\theta_x\cos2\theta_y)\sec^2\theta_y\sec^4\theta_x\tan\theta_x\dot{\theta}_x\dot{\theta}_y + \right.$$

$$(1 + \cos2\theta_x + \cos2\theta_y + \cos2\theta_x\cos2\theta_y)\sec^2\theta_y\sec^4\theta_x\tan\theta_x\tan^2\theta_y\dot{\theta}_x\dot{\theta}_y -$$

$$\left. 2\dot{\theta}_y^2\tan\theta_y\tan^2\theta_x\left(\sec^2\theta_y + \tan^2\theta_x\right)\right] - \frac{g}{l}\frac{\tan\theta_y}{\sec^2\theta_y}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_x\tan\theta_x\tan\theta_y + \tau_y\sec^2\theta_x\right)$$

where $\ddot{\theta}_x$ and $\ddot{\theta}_y$, represent the angular acceleration with reference to x and y axes respectively.

The dynamical equations of the SIP were simulated for the following initial condition: ($\theta_x$=2.3562 rad, $\dot{\theta}_x$=2.01 rad/sec, $\theta_y$=2.3562 rad, $\dot{\theta}_y$=2.01 rad/sec), wherein given a $\dot{\theta}_y$, the $\dot{\theta}_x$ is calculated by making $v_z$=0 in the equation $$v_z = -l\frac{\tan\theta_x\sec^2\theta_x\dot{\theta}_x + \tan\theta_y\sec^2\theta_y\dot{\theta}_y}{\left(1 + \tan^2\theta_x + \tan^2\theta_y\right)^{3/2}},$$

and wherein $v_z$ represents velocity along the z axes, $\theta_x$ and $\theta_y$ being angles of the SIP with respect to the x axis and the y axis respectively and $\dot{\theta}_x$ and $\dot{\theta}_y$ being angular velocity of the SIP respectively. Again the dynamical equations of the SIP were also simulated with changed initial angular velocity of 1.2 rad/sec, the initial condition being: ($\theta_x$=2.3562 rad, $\dot{\theta}_x$=1.2 rad/sec, $\theta_y$=−2.3562 rad, $\dot{\theta}_y$=1.2 rad/sec), to find out $\dot{\theta}_x$ given $\dot{\theta}_y$, $\dot{\theta}_x$ is calculated by making $v_z$=0 in the following equation $$v_z = -l\frac{\tan\theta_x\sec^2\theta_x\dot{\theta}_x + \tan\theta_y\sec^2\theta_y\dot{\theta}_y}{\left(1 + \tan^2\theta_x + \tan^2\theta_y\right)^{3/2}}.$$

The SIP equations were also checked for above the ground scenario by simulating the dynamical equations for the following initial condition: ($\theta_x$=0.0524 rad, $\dot{\theta}_x$=0 rad/sec, $\theta_y$=−0.0354 rad, $\dot{\theta}_y$=0 rad/sec).

In accordance with an embodiment of the present disclosure, the one or more processors 104 are configured to model, at step 306, the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects.

To validate model generated sway characteristics of the present disclosure, experimental data pertaining to the human postural sway, in the form of the COP characteristics of four control subjects in the age group 25 to 40 years having height in the range 5'3" to 5'10", and body weight in the range 50 to 70 kg, when standing bipedally for approximately 30 secs were collected. It was noted from the frequency spectrum of the COP-x signal where |X(k)| is Fourier coefficient corresponds to the $k^{th}$ frequency spectrum, that the frequency spectrum is almost uniformly distributed from 0 to 1 Hz except few peaks at very low frequency component, comparable to DC component. The stated experimental data is also referred later in the description with reference to the description for FIG. 6A through FIG. 6D, FIG. 7A through FIG. 7D, FIG. 8A through FIG. 8D and FIG. 9A through FIG. 9D. To match the human postural sway seen in the control subjects, in accordance with the present disclosure, three additional parameters are introduced in the model. In accordance with the present disclosure, the set of parameters include parameters of the MDP model and the three additional parameters associated with physiology of the human body.

In accordance with an embodiment, the parameters associated with physiology of the human body may include White Gaussian Noise (WGN) added to the generated torque to represent a real world noisy biological system; filtering factor (λ) added to portray signaling characteristics of a neuromuscular junction; and Scaling Factor (SF) introduced to scale down the magnitude of the generated torque for each state of the inverted pendulum after the training of the RL agent is completed, wherein completion of the training is represented by a balanced SIP.

In accordance with an embodiment of the present disclosure, a relationship between the generated torque by the modeled neuronal controller and the torque applied to the dynamical system based on the parameters associated with physiology of the human body is represented as:

$$\tau(t) = \lambda \tau_1(t) + (1 - \lambda)\tau(t-1) \text{ and}$$

$$\tau_{SF}(t) = \frac{\tau(t)}{SF},$$

wherein $\tau_1 = \tau_{NC} + c \times WGN$, $\tau(t)$ represents the torque applied to the dynamical system, $\tau_{SF}(t)$ represents the torque after introducing the Scaling Factor, $\tau_{NC}$ represents the generated torque by the modeled neuronal controller, WGN represents the White Gaussian Noise of magnitude 1, and c represents noise amplitude.

Experimental Results

Figure 6A:
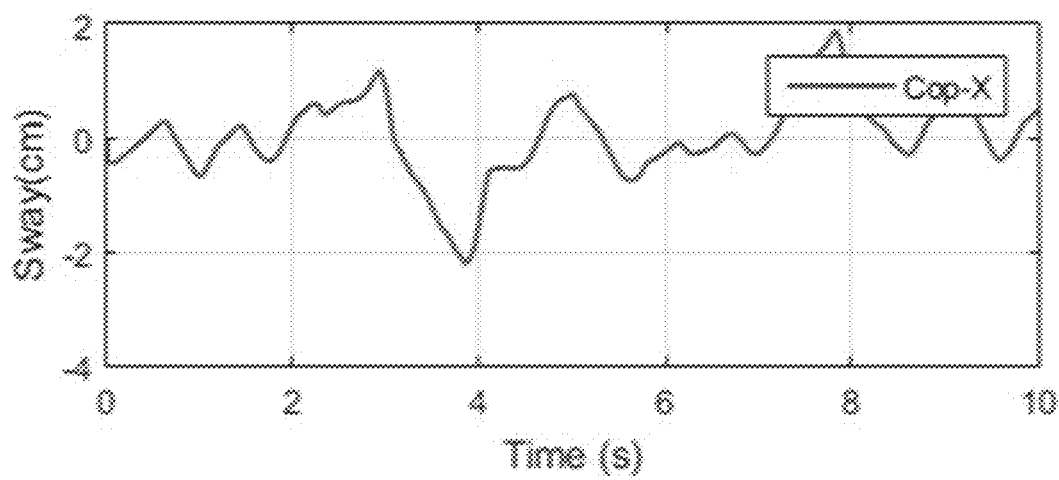
FIG. 6A and FIG. 6B illustrate Center Of Pressure (COP) characteristics along x axis and a corresponding frequency spectrum respectively.
Figure 6B:
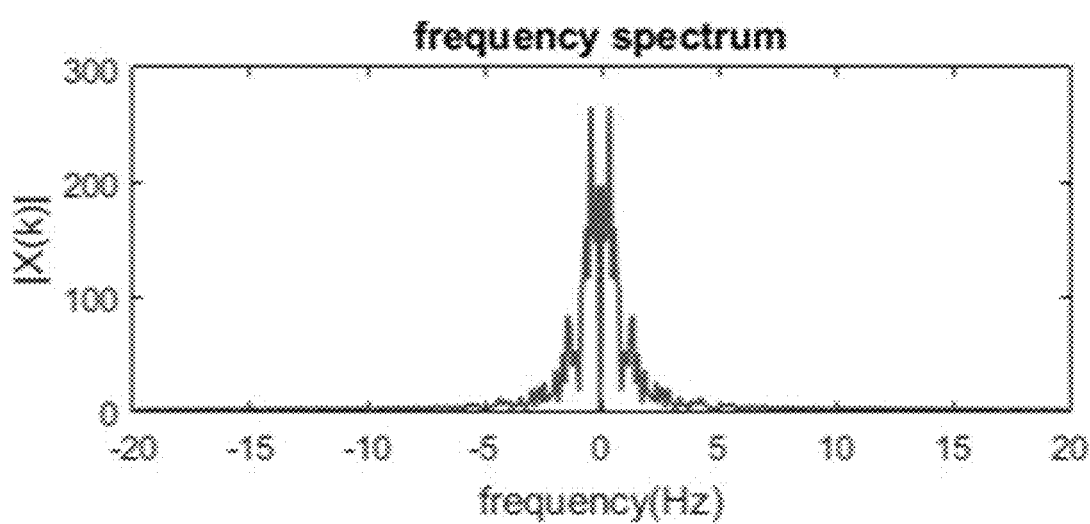
Figure 6C:
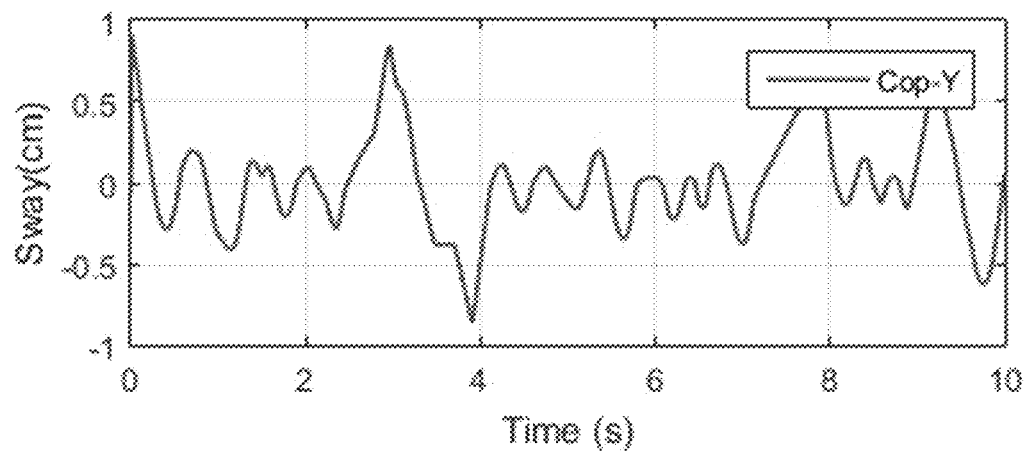
FIG. 6C and FIG. 6D illustrate the COP characteristics along y axis and a corresponding frequency spectrum respectively, for a set of parameters, without introducing parameters associated with physiology of the human body, in accordance with an embodiment of the present disclosure.
Figure 6D:
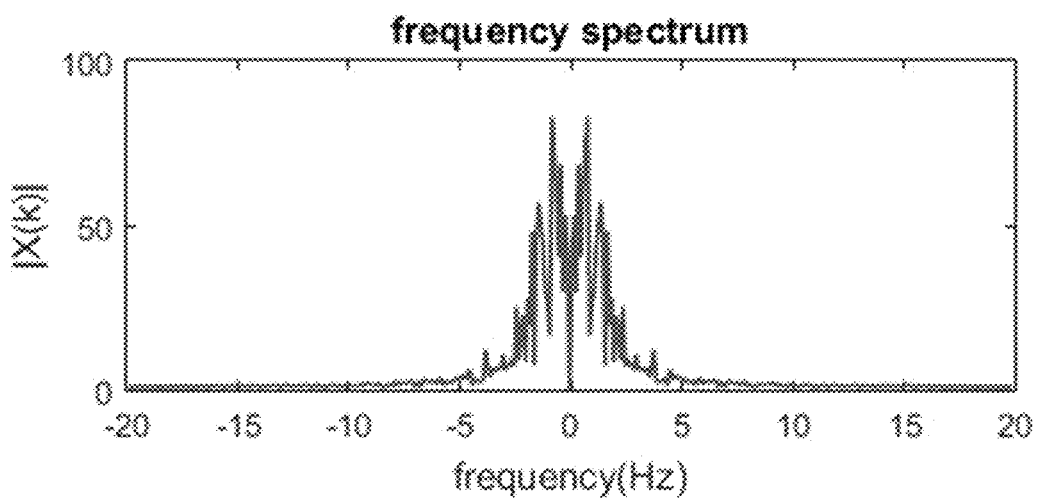

The model sway characteristics were modeled without incorporating the filtering factor, the scaling factor and the noise. The closest human postural sway characteristics generated by the model of the present disclosure are illustrated in FIG. 6A through FIG. 6D and FIG. 7A through FIG. 7D. Particularly, FIG. 6A and FIG. 6B illustrate the COP characteristics along the x axis and a corresponding frequency spectrum while FIG. 6C and FIG. 6D illustrate the COP characteristics along the y axis and a corresponding frequency spectrum for the following set of parameters:

$n_{\theta_x} = 15, n_{\theta_y} = 15;$ $n_{\dot{\theta}_x} = 7, n_{\dot{\theta}_y} = 7, n_{\tau_x} = 9, n_{\tau_y} = 9$ $\tau_{x_{max}} = 500 \text{ Nm}, \tau_{y_{max}} = 500 \text{ Nm},$ $\theta_{x_{max}} = \theta_{y_{max}} = \frac{\pi}{8} \text{ rad}, \dot{\theta}_{x_{max}} = \dot{\theta}_{y_{max}} = 0.3 \text{ rad/s},$ $p_{\theta_x} = 3, p_{\theta_y} = 3, p_{\dot{\theta}_x} = 2, p_{\dot{\theta}_y} = 2, p_{\tau_x} = 3, p_{\tau_y} = 3,$ $\sigma_{\theta_x} = 0.01 \text{ rad}, \sigma_{\theta_y} = 0.01 \text{ rad}, \sigma_{\dot{\theta}_x} = 0.045,$ $\sigma_{\dot{\theta}_y} = 0.045, SF_{\tau_x} = 3, SF_{\tau_y} = 3.$ It may be noted that the frequency spectrum of COP-x is closely matched with the experimental data (detailed above) but the frequency spectrum is twice as spread as the experimental data for COP-y.

Figure 7A:
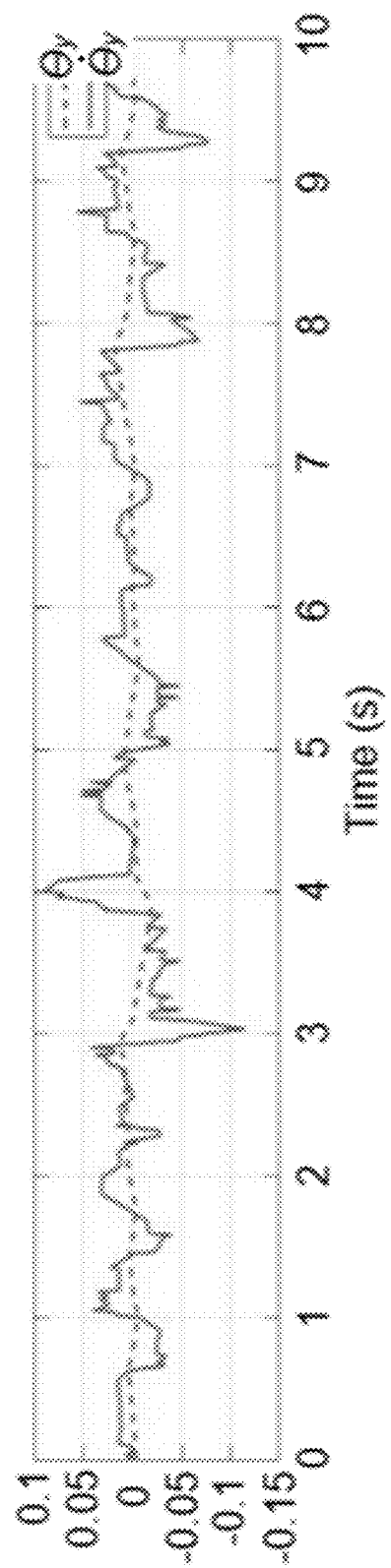
FIG. 7A and FIG. 7B illustrate variance of the angle of the SIP and the angular velocity of the SIP with respect to the x axis and the y axis respectively ($θ_x$, $θ_y$, $\dot{θ}_x$, $\dot{θ}_y$) w.r.t time.
Figure 7B:
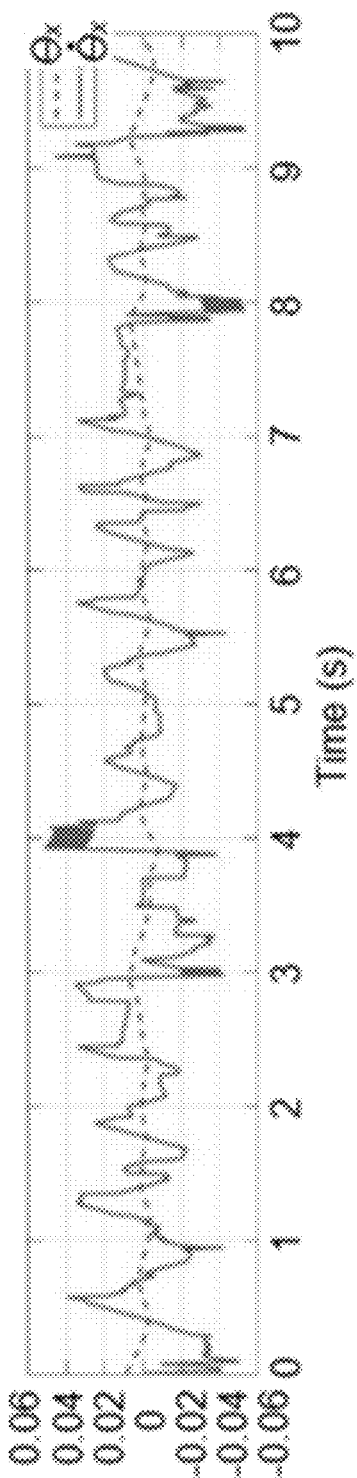
Figure 7C:
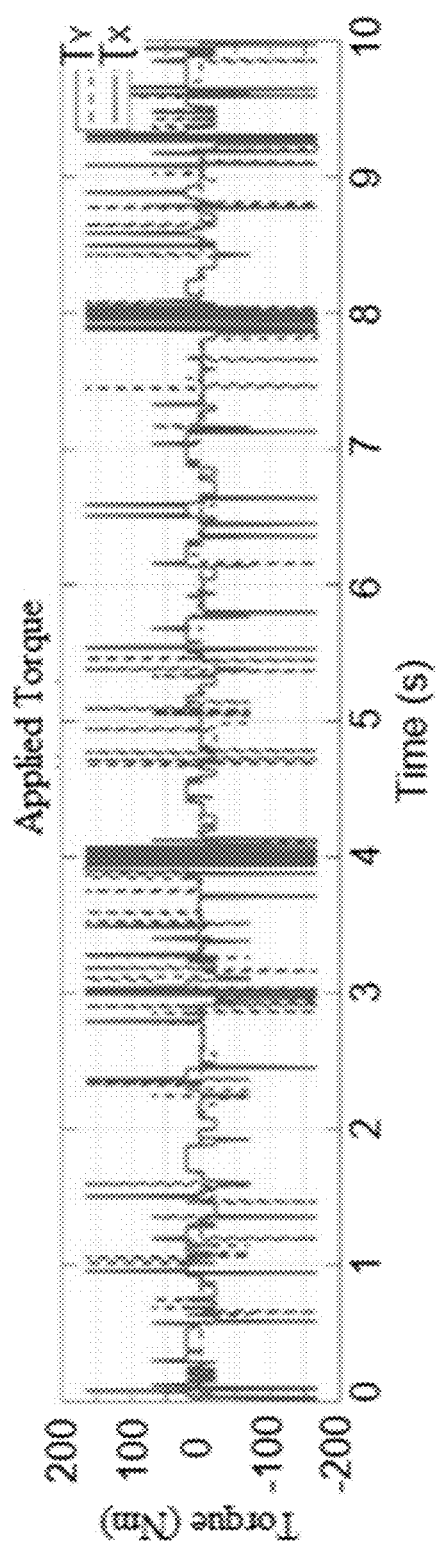
FIG. 7C illustrates a plot of applied torques $τ_x$, $τ_y$ at a pivot joint by the neuronal controller
Figure 7D:
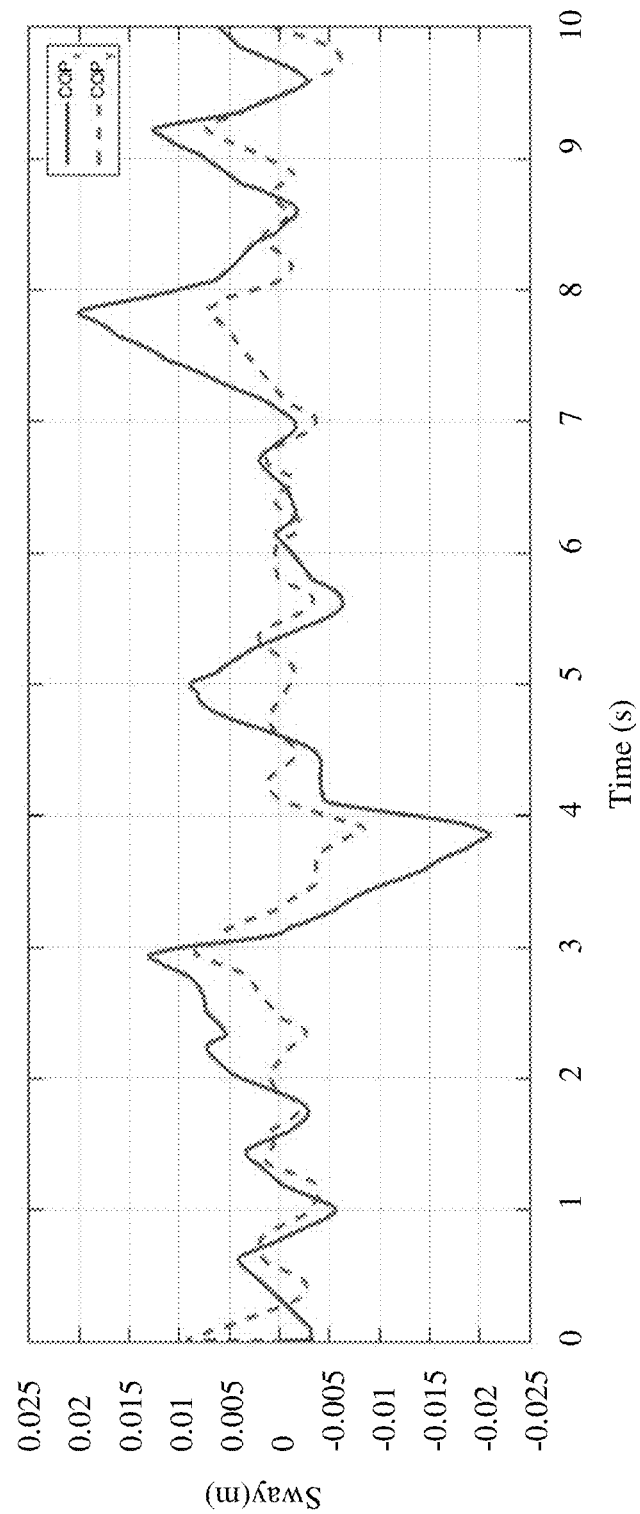
FIG. 7D illustrates COP movement along the x axis and the y axis for the set of parameters referred in FIG. 6A through FIG. 6D.

FIG. 7A and FIG. 7B illustrate variance of the angle of the SIP and the angular velocity of the SIP with respect to the x axis and the y axis respectively ($\theta_x, \theta_y, \dot{\theta}_x, \dot{\theta}_y$) w.r.t time. FIG. 7C illustrates a plot of applied torques $\tau_x, \tau_y$ at the pivot joint by the neuronal controller of the present disclosure. It may be noted that the maximum torque is approximately 166.67 Nm. FIG. 7D illustrates COP movement along the x axis and the y axis with parameter values stated with reference to FIG. 6A through FIG. 6D.

Figure 8A:
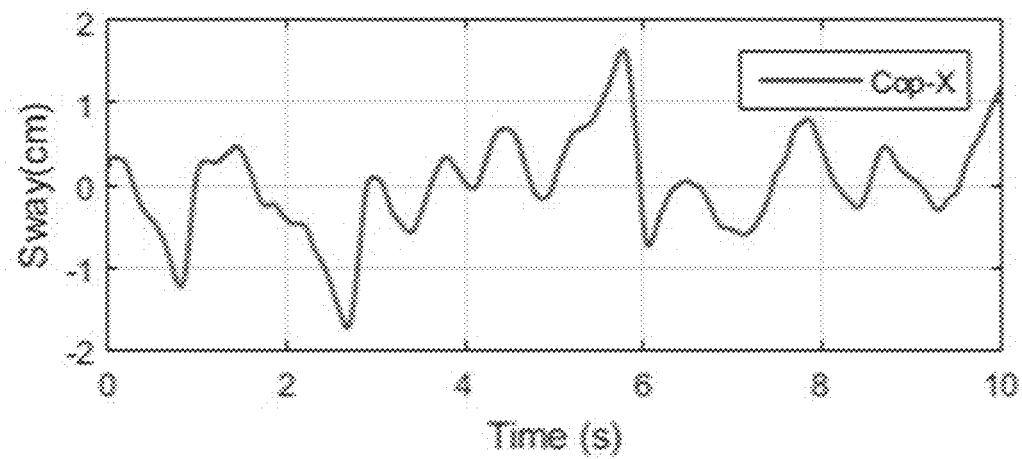
FIG. 8A and FIG. 8B illustrate the COP characteristics along the x axis and a corresponding frequency spectrum respectively.
Figure 8B:
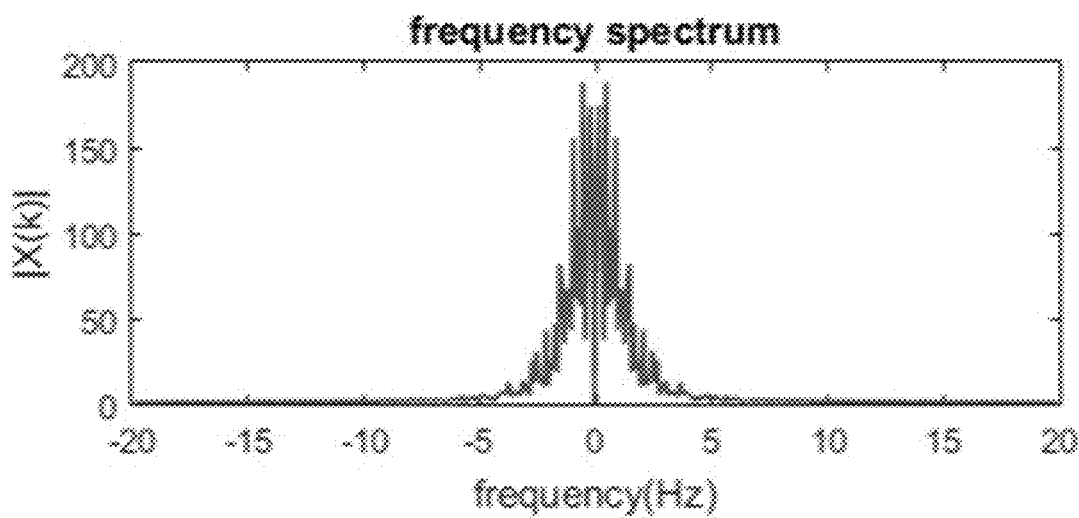
Figure 8C:
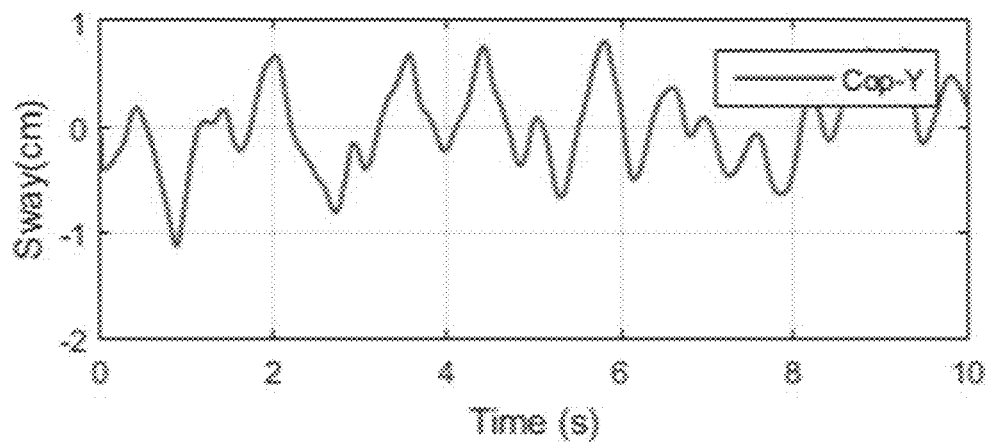
FIG. 8C and FIG. 8D illustrate the COP characteristics along the y axis and a corresponding frequency spectrum respectively, after introducing parameters associated with physiology of the human body, in accordance with an embodiment of the present disclosure.
Figure 8D:
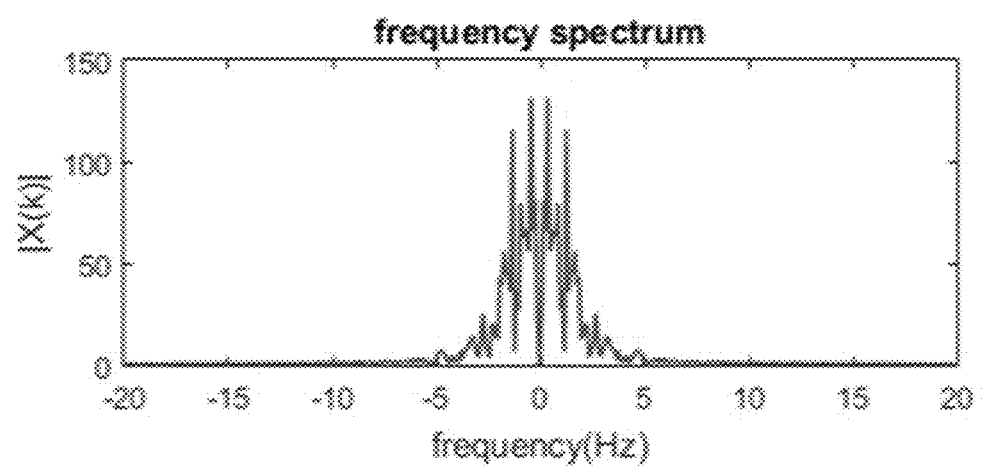
Figure 9A:
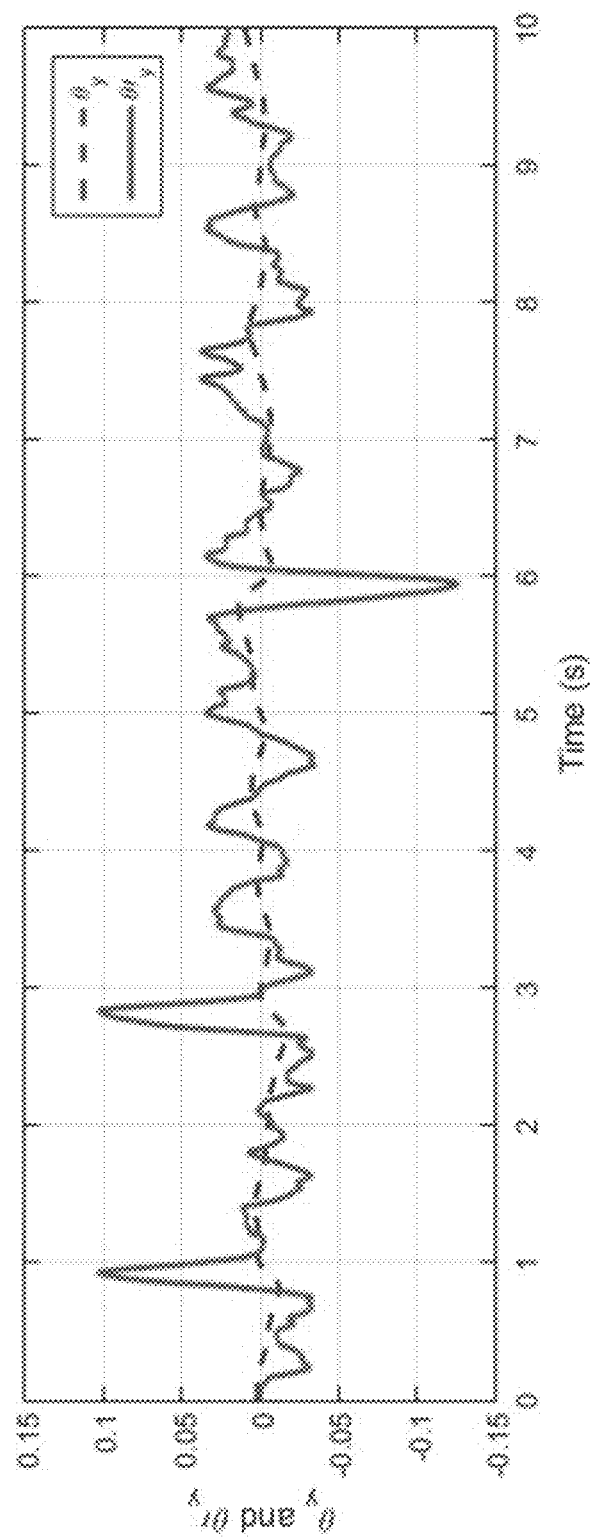
FIG. 9A and FIG. 9B illustrate the variance of the angle of the SIP and the angular velocity of the SIP with respect to the x axis and the y axis respectively ($θ_x$, $θ_y$, $\dot{θ}_x$, $\dot{θ}_y$) w.r.t time.
Figure 9B:
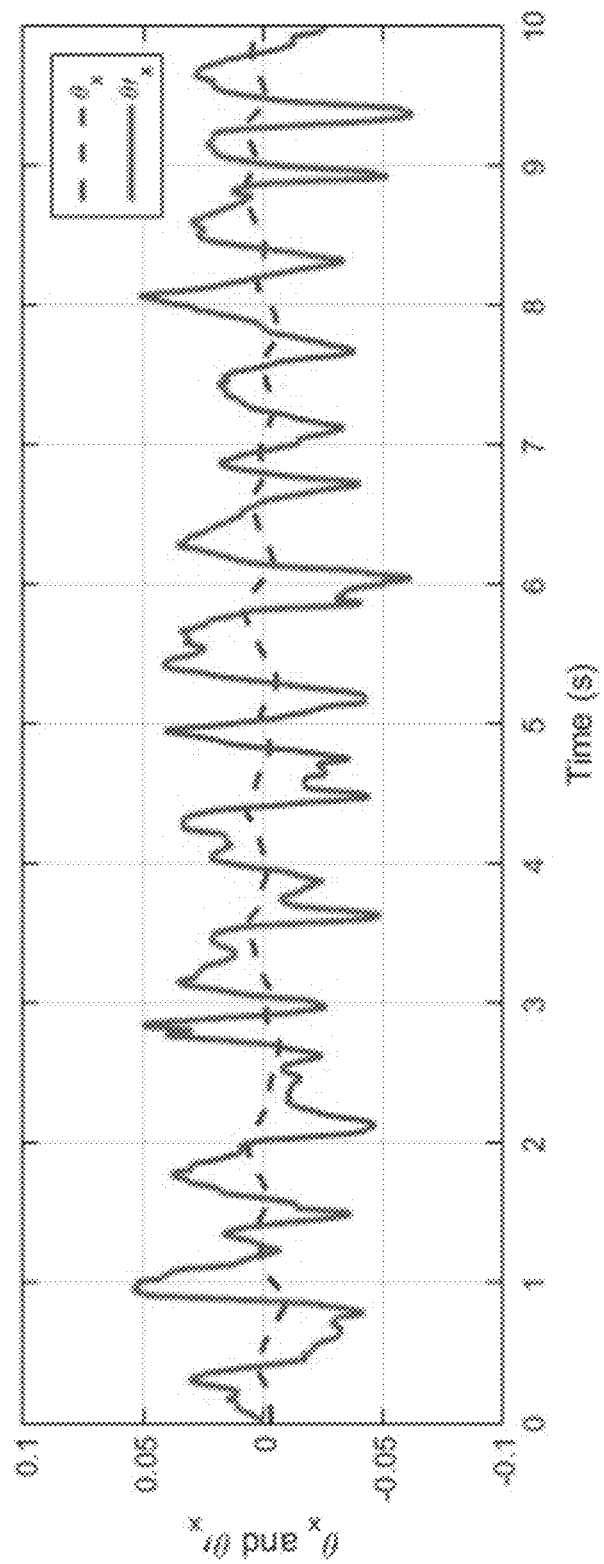
Figure 9C:
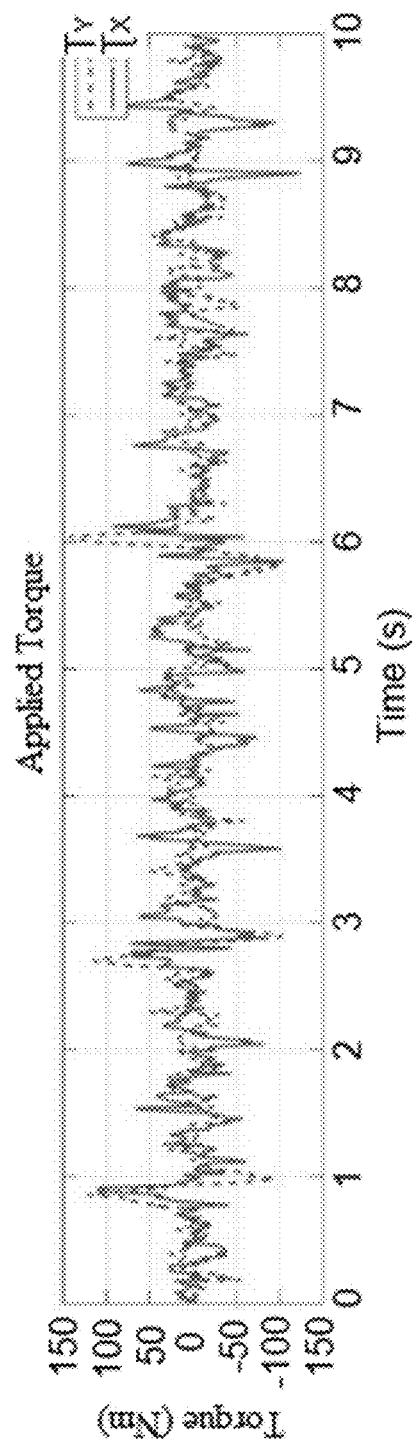
FIG. 9C illustrates a plot of applied torques $τ_x$, $τ_y$ at a pivot joint by the neuronal controller
Figure 9D:
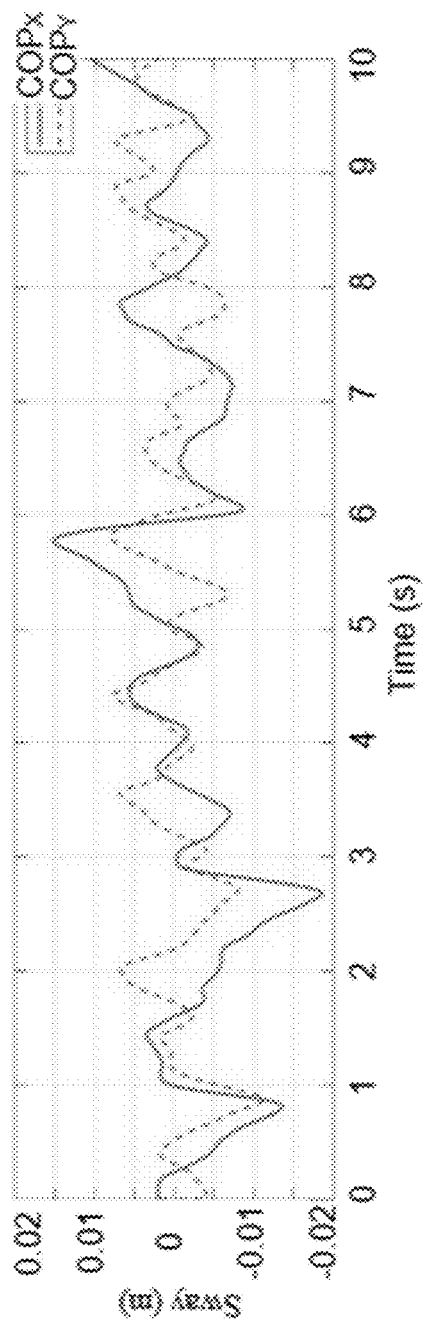
FIG. 9D illustrates COP movement along the x axis and the y axis for the parameters used with reference to FIG. 8A through FIG. 8D.

The additional parameters viz., the filtering factor ($\lambda_{\tau_y}, \lambda_{\tau_x}$), the noise amplitude ($c_{\tau_x}, c_{\tau_y}$) and the scaling factor ($SF_{\tau_y}, SF_{\tau_x}$) were then introduced which resulted in the human postural sway characteristics as seen in the experimental data. After tuning the parameters of the MDP model, the additional parameters and choosing the Reward policy-3 with appropriate standard deviation, the model of the present disclosure produced an expected sway as depicted in FIG. 8A through FIG. 8D and FIG. 9A through FIG. 9D. Particularly, FIGS. 8A and 8B illustrate the COP characteristics along the x axis and a corresponding frequency spectrum while FIG. 8C and FIG. 8D illustrate the COP characteristics along the y axis and a corresponding frequency spectrum. It may be noted that the frequency spectrum is spread between 0 to 1 Hz as observed in the experimental data. FIG. 9A and FIG. 9B illustrate variance of the angle of the SIP and the angular velocity of the SIP with respect to the x axis and the y axis respectively ($\theta_x, \theta_y, \dot{\theta}_x, \dot{\theta}_y$) w.r.t time. FIG. 9C illustrates a plot of applied torques $\tau_x, \tau_y$ at the pivot joint by the neuronal controller of the present disclosure. FIG. 9D illustrates COP movement along the x axis and the y axis with parameter values used with reference to FIG. 8A through FIG. 8D. The illustrated sway characteristics were observed using the following set of parameters:

$n_{\theta_x} = 15, n_{\theta_y} = 15;$ $n_{\dot{\theta}_x} = 7, n_{\dot{\theta}_y} = 7, n_{\tau_x} = 9, n_{\tau_y} = 9$ $\tau_{x_{max}} = 500 \text{ Nm}, \tau_{y_{max}} = 500 \text{ Nm},$ $\theta_{x_{max}} = \theta_{y_{max}} = \frac{\pi}{8} \text{ rad}, \dot{\theta}_{x_{max}} = \dot{\theta}_{y_{max}} = 0.3 \text{ rad/s},$ $p_{\theta_x} = 3, p_{\theta_y} = 3, p_{\dot{\theta}_x} = 2, p_{\dot{\theta}_y} = 2, p_{\tau_x} = 3, p_{\tau_y} = 3,$ $\sigma_{\theta_x} = 0.01 \text{ rad}, \sigma_{\theta_y} = 0.01 \text{ rad}, \sigma_{\dot{\theta}_x} = 0.045,$ $\sigma_{\dot{\theta}_y} = 0.045, \lambda_{\tau_x} = 0.8, \lambda_{\tau_y} = 0.8, SF_{\tau_x} = 3, SF_{\tau_y} = 3,$ $c_{\tau_x} = 7.75 \text{ Nm}, c_{\tau_y} = 7.75 \text{ Nm}.$ In accordance with the present disclosure, by obtaining the COP characteristics of a test subject, using say, a pressure sensing board, a frequency spectrum representative of the postural sway of the test subject may be derived. Accordingly, using the neuronal controller model described above a best set of parameters that correspond to the postural sway of the test subject can be derived. Deviation of the derived set of parameters from those of the one or more control subjects provides insights into balance impairments, if any, associated with the test subject. Thus the mathematical concepts disclosed in the description of the method of the present disclosure are integrated into a practical application of modeling a neuronal controller that exhibits human postural sway so that an analyses of the postural balance of the test subject can be performed and subject specific rehabilitation protocols may be prescribed.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for modeling a neuronal controller exhibiting human postural sway, the method comprising the steps of:

modeling, by one or more hardware processors, the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately;

deriving, by the one or more hardware processors, dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables ($\theta x$ and $\theta y$) being angular deviation of the SIP about a pivot joint and along x and y axes respectively of the global coordinate system, wherein the pivot joint characterizes an ankle joint of the human body; and modeling, by the one or more hardware processors, the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

2. The processor implemented method of claim 1, wherein the Q-learning technique is configured to learn to generate a torque representing an action for each state of the inverted pendulum by:

receiving proprioceptive inputs in the form of angle and angular velocity of the pivot joint of the inverted pendulum; and generating the torque at the pivot joint of the inverted pendulum based on the received proprioceptive inputs to maintain an upright posture of the inverted pendulum.

3. The processor implemented method of claim 1, wherein the step of modeling a neuronal controller comprises reproducing the Center Of Pressure (COP) characteristics in the human body either along the sagittal or along the frontal plane separately in accordance with a dynamical equation based on overall mass of the human body being concentrated at the point of Center Of Mass (COM) located at the $2^{nd}$ lumbar vertebrae of the human body, an approximate height of the $2^{nd}$ lumbar vertebrae, moment of inertia of the inverted pendulum, angle of the inverted pendulum with respect to the direction of gravity, gravitational acceleration, a stiffness constant and a damping constant, wherein the stiffness constant and the damping constant denote pivot joint properties of the inverted pendulum.

4. The processor implemented method of claim 3, wherein the step of modeling a neuronal controller comprises reproducing the Center Of Pressure (COP) characteristics in the human body either along the sagittal or along the frontal plane separately in accordance with the dynamical equation represented as:

$$I\frac{d^2\theta}{dt^2} = \tau + mgL\sin\theta - B\dot{\theta} - K\theta,$$

wherein $I = mL^2$, and wherein m represents overall mass of the human body being concentrated at the point of Center Of Mass (COM) located at the $2^{nd}$ lumbar vertebrae of the human body;

L represents the approximate height of the $2^{nd}$ lumbar vertebrae;

θ represents angle of the inverted pendulum with respect to the direction of gravity;

g represents gravitational acceleration;

I represents moment of inertia of the inverted pendulum;

K represents the stiffness constant; and

B represents the damping constant.

5. The processor implemented method of claim 2, wherein the parameters of the MDP model include:

$n_\theta$ representing resolution of states in θ domain (from $\theta_{max}$ to $-\theta_{max}$);

$n_{\dot\theta}$ representing resolution of states in $\dot\theta$ domain (from $\dot\theta_{max}$ to $-\dot\theta_{max}$);

$n_A$ representing resolution of states in τ domain (from $\tau_{max}$ to $-\tau_{max}$);

$\tau_{max}$ representing the maximum torque exertable on the pivot joint or the boundary of the τ domain;

$\theta_{max}$ representing the boundary of the θ domain;

$\dot\theta_{max}$ representing a finite boundary of the $\dot\theta$ domain;

$p_\alpha$ representing property of a curve from which torque values in the τ domain is sampled;

$p_\theta$ representing property of a curve from which boundaries of states of the θ domain is sampled; and $p_{\dot\theta}$ representing property of a curve from which boundaries of the states of the $\dot\theta$ domain is sampled.

6. The processor implemented method of claim 2, wherein the parameters associated with physiology of the human body include:

White Gaussian Noise (WGN) added to the generated torque to represent a real world noisy biological system;

filtering factor (λ) added to portray signaling characteristics of a neuromuscular junction; and Scaling Factor (SF) introduced to scale down the magnitude of the generated torque for each state of the inverted pendulum after the training of the RL agent is completed, wherein completion of the training is represented by a balanced SIP.

7. The processor implemented method of claim 6, wherein a relationship between the generated torque by the modeled neuronal controller and the torque applied to the dynamical system based on the parameters associated with physiology of the human body is represented as:

$$\tau(t) = \lambda\tau_1(t) + (1-\lambda)\tau(t-1) \text{ and}$$

$$\tau_{SF}(t) = \frac{\tau(t)}{SF},$$

wherein $\tau_1 = \tau_{NC} + c \times WGN$,

τ(t) represents the torque applied to the dynamical system, $\tau_{SF}(t)$ represents the torque after introducing the Scaling Factor, $\tau_{NC}$ represents the generated torque by the modeled neuronal controller, WGN represents the White Gaussian Noise of magnitude 1, and c represents noise amplitude.

8. The processor implemented method of claim 7, wherein the dynamical equations of the SIP are represented as:

for θ=0 to 90°, θ being the polar or zenith angle of the spherical coordinate system, $$\ddot\theta_x = \frac{1}{\left(\sec^2\theta_y + \tan^2\theta_x\right)^2}$$

$$\left[\frac{1}{2}(1 + 3\cos2\theta_x - \cos2\theta_y + \cos2\theta_x\cos2\theta_y)\sec^2\theta_x\sec^4\theta_y\tan\theta_y\dot\theta_x\dot\theta_y + \right.$$

$$(1 + \cos2\theta_x + \cos2\theta_y + \cos2\theta_x\cos2\theta_y)\sec^2\theta_x\sec^4\theta_y\tan\theta_y\tan^2\theta_x\dot\theta_x\dot\theta_y -$$

$$\left.2\dot\theta_x^2\tan\theta_x\tan^2\theta_y\left(\sec^2\theta_y + \tan^2\theta_x\right)\right] + \frac{g}{l}\frac{\tan\theta_x}{\sec^2\theta_x}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_y\tan\theta_x\tan\theta_y + \tau_y\sec^2\theta_y\right), \text{ and}$$

$$\ddot\theta_y = \frac{1}{\left(\sec^2\theta_y + \tan^2\theta_x\right)^2}$$

$$\left[\frac{1}{2}(1 + 3\cos2\theta_y - \cos2\theta_x + \cos2\theta_x\cos2\theta_y)\sec^2\theta_y\sec^4\theta_x\tan\theta_x\dot\theta_x\dot\theta_y + \right.$$

$$(1 + \cos2\theta_x + \cos2\theta_y + \cos2\theta_x\cos2\theta_y)\sec^2\theta_y\sec^4\theta_x\tan\theta_x\tan^2\theta_y\dot\theta_x\dot\theta_y -$$

$$\left.2\dot\theta_y^2\tan\theta_y\tan^2\theta_x\left(\sec^2\theta_y + \tan^2\theta_x\right)\right] + \frac{g}{l}\frac{\tan\theta_y}{\sec^2\theta_y}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_x\tan\theta_x\tan\theta_y + \tau_y\sec^2\theta_x\right); \text{ and for } \theta > 90°,$$

$$\ddot\theta_x = \frac{1}{\left(\sec^2\theta_y + \tan^2\theta_x\right)^2}$$

$$\left[\frac{1}{2}(1 + 3\cos2\theta_x - \cos2\theta_y + \cos2\theta_x\cos2\theta_y)\sec^2\theta_x\sec^4\theta_y\tan\theta_y\dot\theta_x\dot\theta_y + \right.$$

$$(1 + \cos2\theta_x + \cos2\theta_y + \cos2\theta_x\cos2\theta_y)\sec^2\theta_x\sec^4\theta_y\tan\theta_y\tan^2\theta_x\dot\theta_x\dot\theta_y -$$

-continued $$2\dot{\theta}_x^2\tan\theta_x\tan^2\theta_y\left(\sec^2\theta_y+\tan^2\theta_x\right)\right]-\frac{g}{l}\frac{\tan\theta_x}{\sec^2\theta_x}\sqrt{\sec^2\theta_y+\tan^2\theta_x}+$$

$$\frac{\left(\sec^2\theta_y+\tan^2\theta_x\right)}{ml^2\sec^2\theta_x\sec^2\theta_y}\left(\tau_y\tan\theta_x\tan\theta_y+\tau_x\sec^2\theta_y\right) \text{ and}$$

$$\ddot{\theta}_y = \frac{1}{\left(\sec^2\theta_y+\tan^2\theta_x\right)^2}\left[\frac{1}{2}(1+3\cos2\theta_y-\cos2\theta_x+\cos2\theta_x\cos2\theta_y)\right.$$

$$\sec^2\theta_y\sec^4\theta_x\tan\theta_x\dot{\theta}_x\dot{\theta}_y + (1+\cos2\theta_x+\cos2\theta_y+\cos2\theta_x\cos2\theta_y)$$

$$\sec^2\theta_y\sec^4\theta_x\tan\theta_x\tan^2\theta_y\dot{\theta}_x\dot{\theta}_y - 2\dot{\theta}_y^2\tan\theta_y\tan^2\theta_x\left(\sec^2\theta_y+\tan^2\theta_x\right)\right] -$$

$$\frac{g}{l}\frac{\tan\theta_y}{\sec^2\theta_y}\sqrt{\sec^2\theta_y+\tan^2\theta_x} + \frac{\left(\sec^2\theta_y+\tan^2\theta_x\right)}{ml^2\sec^2\theta_x\sec^2\theta_y}\left(\tau_x\tan\theta_x\tan\theta_y+\tau_y\sec^2\theta_x\right)$$

9. A system for modeling a neuronal controller exhibiting human postural sway, the system comprising: one or more data storage devices operatively coupled to one or more hardware processors and configured to store instructions configured for execution by the one or more hardware processors to:
  model the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately;
  derive dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables ($\theta x$ and $\theta y$) being angular deviation of the SIP about a pivot joint and along x and y axes respectively of the global coordinate system, wherein the pivot joint characterizes an ankle joint of the human body; and
  model the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

10. The system of claim 9, wherein the Q-learning technique is configured to learn to generate a torque representing an action for each state of the inverted pendulum by:
  receiving proprioceptive inputs in the form of angle and angular velocity of the pivot joint of the inverted pendulum; and
  generating the torque at the pivot joint of the inverted pendulum based on the received proprioceptive inputs to maintain an upright posture of the inverted pendulum.

11. The system of claim 9, wherein the one or more hardware processors are configured to perform the step of modeling a neuronal controller by reproducing the Center Of Pressure (COP) characteristics in the human body either along the sagittal or along the frontal plane separately in accordance with a dynamic equation based on overall mass m of the human body being concentrated at the point of Center Of Mass (COM) located at the $2^{nd}$ lumbar vertebrae of the human body, an approximate height L of the $2^{nd}$ lumbar vertebrae, moment of inertia of the inverted pendulum I, angle of the inverted pendulum $\theta$ with respect to the direction of gravity, gravitational acceleration g, a stiffness constant K and a damping constant B, wherein the stiffness constant and the damping constant denote pivot joint properties of the inverted pendulum.

12. The system of claim 11, wherein the parameters of the MDP model include:
  $n_\theta$ representing resolution of states in $\theta$ domain (from $\theta_{max}$ to $-\theta_{max}$);
  $n_{\dot{\theta}}$ representing resolution of states in $\dot{\theta}$ domain (from $\dot{\theta}_{max}$ to $-\dot{\theta}_{max}$);
  $n_A$ representing resolution of states in $\tau$ domain (from $\tau_{max}$ to $-\tau_{max}$);
  $\tau_{max}$ representing the maximum torque exertable on the pivot joint or the boundary of the $\tau$ domain;
  $\theta_{max}$ representing the boundary of the $\theta$ domain;
  $\dot{\theta}_{max}$ representing a finite boundary of the $\dot{\theta}$ domain;
  $p_\alpha$ representing property of a curve from which torque values in the $\tau$ domain is sampled;
  $p_\theta$ representing property of a curve from which boundaries of states of the $\theta$ domain is sampled; and
  $p_{\dot{\theta}}$ representing property of a curve from which boundaries of the states of the $\dot{\theta}$ domain is sampled; and
the parameters associated with physiology of the human body include:
  White Gaussian Noise (WGN) added to the generated torque to represent a real world noisy biological system;
  filtering factor ($\lambda$) added to portray signaling characteristics of a neuromuscular junction; and
  Scaling Factor (SF) introduced to scale down the magnitude of the generated torque for each state of the inverted pendulum after the training of the RL agent is completed, wherein completion is of the training is represented by a balanced SIP.

13. The system of claim 12, wherein a relationship between the generated torque by the modeled neuronal controller and the torque applied to the dynamical system based on the parameters associated with physiology of the human body is represented as:

$$\tau(t) = \lambda\tau_1(t) + (1-\lambda)\tau(t-1),$$

$$\tau_{SF}(t) = \frac{\tau(t)}{SF}$$

wherein $\tau_1 = \tau_{NC} + c \times WGN$,
$\tau(t)$ represents the torque applied to the dynamical system,
$\tau_{SF}(t)$ represents the torque after introducing the Scaling Factor,
$\tau_{NC}$ represents the generated torque by the modeled neuronal controller,
WGN represents the White Gaussian Noise of magnitude 1, and
c represents noise amplitude.

14. The system of claim 13, wherein the dynamical equations of the SIP are represented as:

for θ=0 to 90°, θ being the polar or zenith angle of the spherical coordinate system, $$\ddot{\theta}_x = \frac{1}{\left(\sec^2\theta_y + \tan^2\theta_x\right)^2}$$

$$\left[\frac{1}{2}(1 + 3\cos 2\theta_x - \cos 2\theta_y + \cos 2\theta_x \cos 2\theta_y)\sec^2\theta_x \sec^4\theta_y \tan\theta_y \dot{\theta}_x \dot{\theta}_y + \right.$$

$$(1 + \cos 2\theta_x + \cos 2\theta_y + \cos 2\theta_x \cos 2\theta_y)\sec^2\theta_x \sec^4\theta_y \tan\theta_y \tan^2\theta_x \dot{\theta}_x \dot{\theta}_y - $$

$$\left. 2\dot{\theta}_x^2 \tan\theta_x \tan^2\theta_y \left(\sec^2\theta_y + \tan^2\theta_x\right)\right] + \frac{g}{l}\frac{\tan\theta_x}{\sec^2\theta_x}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_y\tan\theta_x\tan\theta_y + \tau_x\sec^2\theta_y\right), \text{ and}$$

$$\ddot{\theta}_y = \frac{1}{\left(\sec^2\theta_y + \tan^2\theta_x\right)^2}\left[\frac{1}{2}(1 + 3\cos 2\theta_y - \cos 2\theta_x + \cos 2\theta_x \cos 2\theta_y)\right.$$

$$\sec^2\theta_y \sec^4\theta_x \tan\theta_x \dot{\theta}_x \dot{\theta}_y + (1 + \cos 2\theta_x + \cos 2\theta_y + \cos 2\theta_x \cos 2\theta_y)$$

$$\left.\sec^2\theta_y \sec^4\theta_x \tan\theta_x \tan^2\theta_y \dot{\theta}_x \dot{\theta}_y - 2\dot{\theta}_y^2 \tan\theta_y \tan^2\theta_x \left(\sec^2\theta_y + \tan^2\theta_x\right)\right] +$$

$$\frac{g}{l}\frac{\tan\theta_y}{\sec^2\theta_y}\sqrt{\sec^2\theta_y + \tan^2\theta_x} + \frac{\left(\sec^2\theta_y + \tan^2\theta_x\right)}{ml^2\sec^2\theta_x \sec^2\theta_y}; \text{ and for } \theta > 90°,$$

$$\ddot{\theta}_x = \frac{1}{\left(\sec^2\theta_y + \tan^2\theta_x\right)^2}$$

$$\left[\frac{1}{2}(1 + 3\cos 2\theta_x - \cos 2\theta_y + \cos 2\theta_x \cos 2\theta_y)\sec^2\theta_x \sec^4\theta_y \tan\theta_y \dot{\theta}_x \dot{\theta}_y + \right.$$

$$(1 + \cos 2\theta_x + \cos 2\theta_y + \cos 2\theta_x \cos 2\theta_y)\sec^2\theta_x \sec^4\theta_y \tan\theta_y \tan^2\theta_x \dot{\theta}_x \dot{\theta}_y - $$

$$\left. 2\dot{\theta}_x^2 \tan\theta_x \tan^2\theta_y \left(\sec^2\theta_y + \tan^2\theta_x\right)\right] - \frac{g}{l}\frac{\tan\theta_x}{\sec^2\theta_x}\sqrt{\sec^2\theta_y + \tan^2\theta_x} +$$

$$\frac{\left(\sec^2\theta_y + \tan^2\theta_x\right)}{ml^2\sec^2\theta_x\sec^2\theta_y}\left(\tau_y\tan\theta_x\tan\theta_y + \tau_x\sec^2\theta_y\right) \text{ and}$$

$$\ddot{\theta}_y = \frac{1}{\left(\sec^2\theta_y + \tan^2\theta_x\right)^2}\left[\frac{1}{2}(1 + 3\cos 2\theta_y - \cos 2\theta_x + \cos 2\theta_x \cos 2\theta_y)\right.$$

$$\sec^2\theta_y \sec^4\theta_x \tan\theta_x \dot{\theta}_x \dot{\theta}_y + (1 + \cos 2\theta_x + \cos 2\theta_y + \cos 2\theta_x \cos 2\theta_y)$$

$$\left.\sec^2\theta_y \sec^4\theta_x \tan\theta_x \tan^2\theta_y \dot{\theta}_x \dot{\theta}_y - 2\dot{\theta}_y^2 \tan\theta_y \tan^2\theta_x \left(\sec^2\theta_y + \tan^2\theta_x\right)\right] -$$

$$\frac{g}{l}\frac{\tan\theta_y}{\sec^2\theta_y}\sqrt{\sec^2\theta_y + \tan^2\theta_x} + \frac{\left(\sec^2\theta_y + \tan^2\theta_x\right)}{ml^2\sec^2\theta_x\sec^2\theta_y}\left(\tau_x\tan\theta_x\tan\theta_y + \tau_y\sec^2\theta_x\right).$$

15. A computer program product comprising a non-transitory computer readable medium having a computer readable program embodied therein, wherein the computer readable program, when executed on a computing device, causes the computing device to:

model the neuronal controller in the form of a Reinforcement Learning (RL) agent based on an inverted pendulum with 1 Degree Of Freedom (1 DOF) representing a first mechanical model of a human body in the form of a dynamical system, wherein the RL agent is trained using a Q-learning technique to learn an optimal state-action value (Q-value) function for a tuneable Markov Decision Process (MDP) model, wherein the modeled neuronal controller is configured to reproduce Center Of Pressure (COP) characteristics in the human body either along a sagittal plane or along a frontal plane separately;

derive dynamical equations of a Spherical Inverted Pendulum (SIP) with respect to a global coordinate system, wherein the SIP represents a second mechanical model of the human body that exhibits postural sway along both the frontal plane and the sagittal plane together, wherein the dynamical equations are derived by using Lagrange's equations with two independent state variables (θx and θy) being angular deviation of the SIP about a pivot joint and along x and y axes respectively of the global coordinate system, wherein the pivot joint characterizes an ankle joint of the human body; and model the human postural sway both along the sagittal plane and along the frontal plane together using the modeled neuronal controller and the derived dynamical equations of the SIP by tuning (i) a reward function comprised in the modeled neuronal controller and (ii) a set of parameters to balance the SIP such that the postural sway characteristics generated by the modeled neuronal controller match the postural sway characteristics of one or more control subjects, wherein the set of parameters include parameters of the MDP model and parameters associated with physiology of the human body.

* * * * *